(12) United States Patent
Xu

(10) Patent No.: US 11,331,066 B2
(45) Date of Patent: May 17, 2022

(54) IMAGING METHOD AND SYSTEM FOR DETERMINING A SCAN AREA

(71) Applicant: SHANGHAI UNITED IMAGING HEALTHCARE CO., LTD., Shanghai (CN)

(72) Inventor: Tianyi Xu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 168 days.

(21) Appl. No.: 16/568,498

(22) Filed: Sep. 12, 2019

(65) Prior Publication Data

US 2020/0000421 A1 Jan. 2, 2020

Related U.S. Application Data

(63) Continuation of application No. 16/022,877, filed on Jun. 29, 2018, now Pat. No. 10,413,261, which is a
(Continued)

(30) Foreign Application Priority Data

Dec. 30, 2016 (CN) .......................... 201611256670.5

(51) Int. Cl.
*A61B 6/00* (2006.01)
*A61B 6/03* (2006.01)
(Continued)

(52) U.S. Cl.
CPC .............. *A61B 6/545* (2013.01); *A61B 6/032* (2013.01); *A61B 6/035* (2013.01); *A61B 6/037* (2013.01);
(Continued)

(58) Field of Classification Search
CPC ........... A61B 6/03; A61B 6/032; A61B 6/037; A61B 6/467; A61B 6/469; A61B 6/488;
(Continued)

(56) References Cited

U.S. PATENT DOCUMENTS 5,379,333 A * 1/1995 Toth ........................ A61B 6/032
378/108
5,400,378 A * 3/1995 Toth ........................ A61B 6/032
378/108
(Continued)

FOREIGN PATENT DOCUMENTS

CN 101627917 A 1/2010
CN 103385728 A 11/2013
(Continued)

OTHER PUBLICATIONS

First Office Action in Chinese Application No. 201611256670.5 dated May 28, 2019, 8 pages.
(Continued)

*Primary Examiner* — Allen C. Ho
(74) *Attorney, Agent, or Firm* — Metis IP LLC

(57) ABSTRACT

A system includes a storage device storing a set of instructions and at least one processor in communication with the storage device, wherein when executing the instructions, the at least one processor is configured to cause the system to determine a first scan area on a scanning object. The system may also acquire raw data generated by scanning the first scan area on the scanning object and generate a positioning image based on the raw data. The system may also generate a pixel value distribution curve based on the positioning image, and determine a second scan area on the scanning object based on the pixel value distribution curve. The system may also scan the second scan area on the scanning object.

20 Claims, 17 Drawing Sheets

Related U.S. Application Data continuation of application No. PCT/CN2017/120342, filed on Dec. 29, 2017.

(51) Int. Cl.
*G06T 11/00* (2006.01)
*G06T 7/194* (2017.01)
*G06T 7/00* (2017.01)

(52) U.S. Cl.
CPC .............. *A61B 6/44* (2013.01); *A61B 6/4417* (2013.01); *A61B 6/46* (2013.01); *A61B 6/467* (2013.01); *A61B 6/469* (2013.01); *A61B 6/488* (2013.01); *A61B 6/52* (2013.01); *A61B 6/5205* (2013.01); *A61B 6/5235* (2013.01); *A61B 6/5247* (2013.01); *A61B 6/54* (2013.01); *A61B 6/542* (2013.01); *A61B 6/544* (2013.01); *G06T 7/0012* (2013.01); *G06T 7/194* (2017.01); *G06T 11/005* (2013.01); *A61B 6/4411* (2013.01); *G06T 2207/10081* (2013.01); *G06T 2207/20016* (2013.01); *G06T 2211/412* (2013.01)

(58) Field of Classification Search
CPC ........... A61B 6/52; A61B 6/5205; A61B 6/54; A61B 6/542; A61B 6/544; A61B 6/545; A61B 6/46
USPC ................ 378/16, 20, 62, 108–112
See application file for complete search history.

(56) References Cited

U.S. PATENT DOCUMENTS

| | | | |
|---|---|---|---|
| 5,450,462 A * | 9/1995 | Toth | A61B 6/032 378/108 |
| 5,485,494 A * | 1/1996 | Williams | A61B 6/032 378/110 |
| 5,625,662 A * | 4/1997 | Toth | H05G 1/26 378/108 |
| 5,696,807 A * | 12/1997 | Hsieh | A61B 6/032 378/109 |
| 5,822,393 A * | 10/1998 | Popescu | A61B 6/032 378/108 |
| 5,867,555 A * | 2/1999 | Popescu | G01N 23/046 378/16 |
| 5,949,811 A * | 9/1999 | Baba | A61B 6/542 378/108 |
| 6,385,280 B1 * | 5/2002 | Bittl | A61B 6/032 378/106 |
| 6,463,121 B1 | 10/2002 | Milnes | |
| 6,490,337 B1 * | 12/2002 | Nagaoka | A61B 6/032 378/16 |
| 6,507,639 B1 * | 1/2003 | Popescu | A61B 6/032 378/108 |
| 6,744,846 B2 * | 6/2004 | Popescu | A61B 6/032 378/16 |
| 6,754,301 B2 * | 6/2004 | Horiuchi | A61B 6/032 378/16 |
| 6,775,352 B2 * | 8/2004 | Toth | A61B 6/032 378/101 |
| 6,904,127 B2 * | 6/2005 | Toth | A61B 6/032 378/108 |
| 6,987,828 B2 * | 1/2006 | Horiuchi | G01N 23/046 378/108 |
| 6,990,175 B2 | 1/2006 | Nakashima et al. | |
| 7,039,163 B2 * | 5/2006 | Popescu | A61B 6/032 378/109 |
| 7,042,977 B2 * | 5/2006 | Dafni | A61B 6/032 378/16 |
| 7,082,183 B2 * | 7/2006 | Toth | A61B 6/032 378/16 |
| 7,103,139 B2 * | 9/2006 | Nagaoka | A61B 6/032 378/16 |
| 7,106,824 B2 * | 9/2006 | Kazama | A61B 6/032 378/110 |
| 7,113,569 B2 * | 9/2006 | Okumura | A61B 6/032 378/150 |
| 7,142,630 B2 * | 11/2006 | Suzuki | A61B 6/032 378/16 |
| 7,145,982 B2 * | 12/2006 | Ikeda | A61B 6/032 378/16 |
| 7,203,270 B2 * | 4/2007 | Okumura | A61B 6/032 378/109 |
| 7,215,733 B2 * | 5/2007 | Nabatame | A61B 6/032 378/110 |
| 7,336,762 B2 * | 2/2008 | Seto | A61B 6/032 378/110 |
| 7,515,678 B2 | 4/2009 | Hsieh et al. | |
| 7,522,701 B2 | 4/2009 | Jensen et al. | |
| 7,602,880 B2 * | 10/2009 | Hirokawa | A61B 6/032 378/108 |
| 7,636,416 B2 * | 12/2009 | Miyazaki | A61B 6/542 378/108 |
| 7,668,286 B2 * | 2/2010 | Tsuyuki | A61B 6/0487 378/8 |
| 7,715,522 B2 * | 5/2010 | Goto | A61B 6/542 378/16 |
| 7,734,006 B2 * | 6/2010 | Miyazaki | A61B 6/542 378/8 |
| 7,778,381 B2 * | 8/2010 | Nishide | A61B 6/4085 378/4 |
| 7,945,013 B2 * | 5/2011 | Goto | A61B 6/50 378/16 |
| 7,983,457 B2 * | 7/2011 | Toth | A61B 6/032 382/128 |
| 8,005,187 B2 | 8/2011 | Suzuki et al. | |
| 8,009,794 B2 | 8/2011 | Partain | |
| 8,031,831 B2 * | 10/2011 | Zou | A61B 6/032 378/16 |
| 8,068,650 B2 | 11/2011 | Kumar et al. | |
| 8,081,809 B2 | 12/2011 | Dutta et al. | |
| 8,175,217 B2 * | 5/2012 | Sugaya | H05G 1/30 378/16 |
| 8,194,821 B2 * | 6/2012 | Seppi | G21K 1/10 378/62 |
| 8,229,059 B2 * | 7/2012 | Mukumoto | A61B 6/542 378/4 |
| 8,548,122 B2 | 10/2013 | Hay et al. | |
| 8,649,480 B2 * | 2/2014 | Yoshida | A61B 6/032 378/16 |
| 8,693,760 B2 * | 4/2014 | Yokosawa | G01R 33/4833 382/131 |
| 8,744,039 B2 * | 6/2014 | Hirokawa | G16H 50/30 378/16 |
| 8,848,860 B2 * | 9/2014 | Yazaki | H05G 1/34 378/8 |
| 9,295,434 B2 | 3/2016 | Herold | |
| 9,420,976 B2 | 8/2016 | Jackson et al. | |
| 9,710,141 B2 | 7/2017 | Braun et al. | |
| 9,779,520 B2 | 10/2017 | Suzuki | |
| 9,858,705 B2 | 1/2018 | Wiemker et al. | |
| 9,924,916 B2 | 3/2018 | Kato et al. | |
| 9,949,711 B2 | 4/2018 | Goto et al. | |
| 9,980,690 B2 | 5/2018 | Muroi et al. | |
| 10,007,973 B2 | 6/2018 | Nakano | |
| 10,028,717 B2 | 7/2018 | Lou et al. | |
| 10,045,754 B2 | 8/2018 | Klinder et al. | |
| 10,052,078 B2 | 8/2018 | Brendel et al. | |
| 10,080,538 B2 | 9/2018 | Hofmann et al. | |
| 10,092,256 B2 | 10/2018 | Yorkston et al. | |
| 10,101,284 B2 | 10/2018 | Koike et al. | |
| 10,105,118 B2 | 10/2018 | Jung et al. | |
| 10,123,763 B2 | 11/2018 | Kondo | |
| 10,130,320 B2 | 11/2018 | Saito et al. | |
| 10,413,261 B2 * | 9/2019 | Xu | A61B 6/545 |
| 10,945,697 B2 * | 3/2021 | Goto | A61B 6/027 |
| 2002/0072665 A1 | 6/2002 | Ozaki | |
| 2007/0003002 A1 | 1/2007 | Chen et al. | |

(56) References Cited

U.S. PATENT DOCUMENTS

| | | |
|---|---|---|
| 2012/0093385 A1 | 4/2012 | Yokosawa et al. |
| 2014/0185740 A1 | 7/2014 | Chen et al. |
| 2016/0157812 A1 | 6/2016 | Jung et al. |
| 2018/0317873 A1 | 11/2018 | Xu |

FOREIGN PATENT DOCUMENTS

| | | |
|---|---|---|
| CN | 103400398 A | 11/2013 |
| CN | 104337535 A | 2/2015 |
| CN | 105078495 A | 11/2015 |
| CN | 105433971 A | 3/2016 |

OTHER PUBLICATIONS

International Search Report in PCT/CN2017/120342 dated Mar. 28, 2018, 5 pages.
Written Opinion in PCT/CN2017/120342 dated Mar. 28, 2018, 5 pages.
The Extended European Search Report in European Application No. 17885960.9 dated Dec. 19, 2019, 7 pages.

* cited by examiner

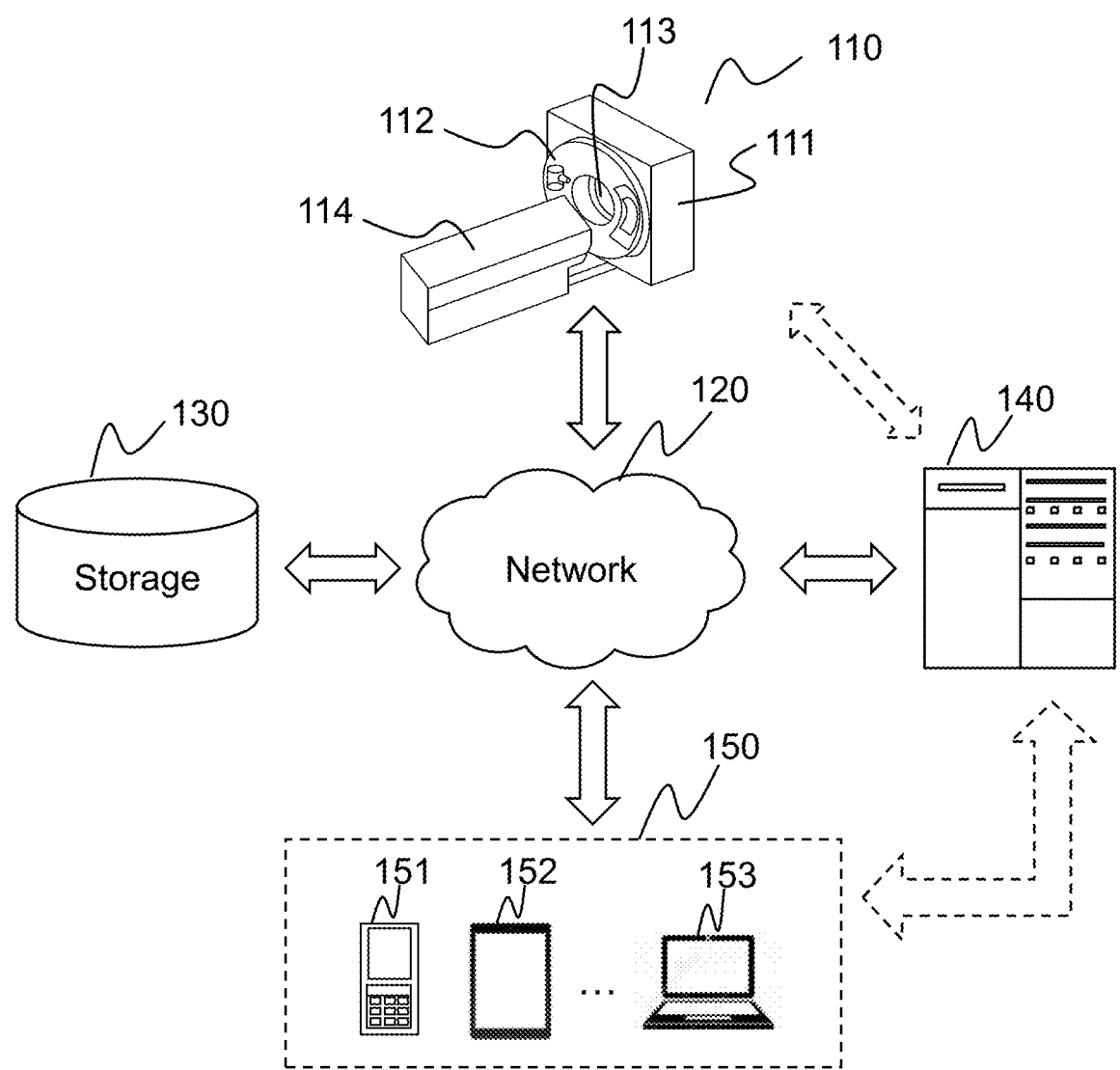
FIG. 1-A

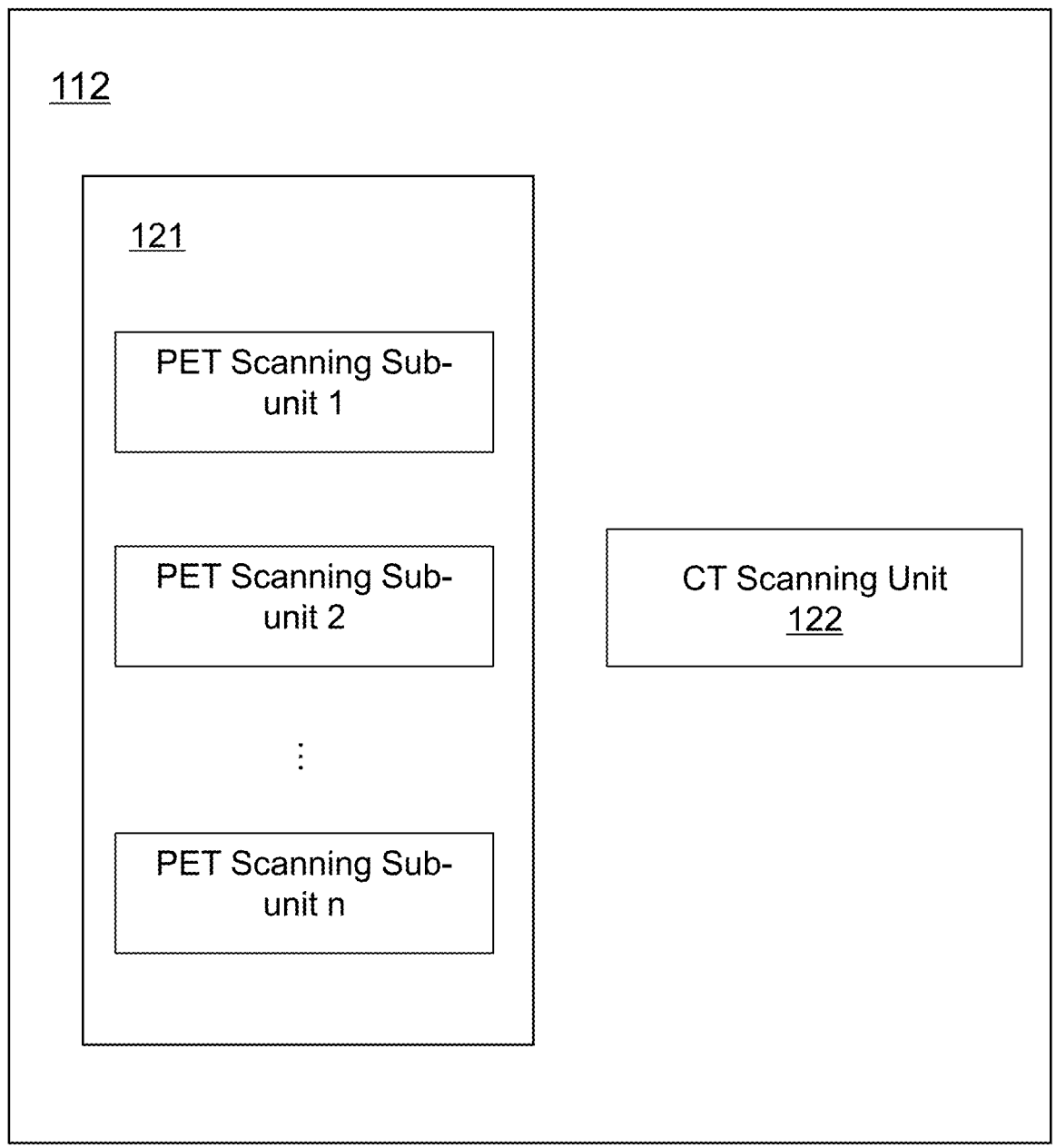
FIG. 1-B

420

First Scan Area Determination Unit
502

Acquisition Unit
504

Reconstruction Unit
506

Distribution Curve Generation Unit
508

Second Scan Area Determination Unit
510

Control Unit
512

Curvature Determination Sub-unit
1002

Curvature Point Determination Sub-unit
1004

Scan Area Determination Sub-unit
1006

FIG. 10

Prior art

IMAGING METHOD AND SYSTEM FOR DETERMINING A SCAN AREA

This application is a continuation application of U.S. patent application Ser. No. 16/022,877, filed on Jun. 29, 2018, now U.S. Pat. No. 10,413,261 B2 issued on Sep. 17, 2019, which is a continuation application of International Application No. PCT/CN2017/120342, filed on Dec. 29, 2017, which claims priority of Chinese Application No. 201611256670.5, filed on Dec. 30, 2016, the contents of each of which are incorporated herein by reference.

TECHNICAL FIELD

The application generally relates to method and system for imaging scanning, and more specifically relates to method and system for determining scan area based on a positioning image.

BACKGROUND

Generally, a positioning image is necessary to determine a scanning range and a location of image reconstruction before an imaging system scanning a patient. And then the imaging system scans the parts to be examined of the patient to obtain original data for image reconstruction to generate a medical image.

Taking the Positron Emission Tomography/Computed Tomography (PET/CT) system as an example, before the system performs imaging scanning, usually the system performs a positioning scanning to the patient to obtain a CT positioning image, and then a scanning area (i.e., an area of interest) may be determined based on the positioning image by a user, as the area to be reconstructed. Refer to FIG. 15, which illustrates an exemplary positioning image obtained after scanning the area to be imaged. On the interface where the positioning image is displayed, a rectangular frame representing the scan area 10 is drawn on the positioning image by dragging a mouse by a user. After dragging, the scan area 10 is determined. Organs or issues to be examined may be in the scan area 10 and the system may perform scanning and reconstruction based on the scan area 10 thus the rest of the patient may be free from scanning.

The above-mentioned manual adjustment of the scan range setting has a lot of shortcomings. Firstly, to manually adjust the scope of the scan range is often not accurate enough, and thus produce unnecessary CT dose. Secondly, manually adjusting the scope of the scan range spends long time, resulting in the extension of the entire scanning process time and reducing the efficiency of the scan. Further, the extension of the scanning process may increase the patient's physical and psychological burden.

SUMMARY

According to an aspect of the present disclosure, a system is provided. The system may comprise a storage device and at least one processor in communication with the storage device. The storage device may store a set of instructions. When executing the set of instructions, the at least one processor may be configured to cause the system to perform one or more of the following operations. The at least one processor may be configured to cause the system to determine a first scan area on a scanning object. The at least one processor may be configured to cause the system to acquire raw data generated by scanning the first scan area on the scanning object and generate a positioning image based on the raw data. The at least one processor may also be configured to cause the system to generate a pixel value distribution curve based on the positioning image and determine a second scan area on the scanning object based on the pixel value distribution curve. Then the at least one processor may also be configured to cause the system to scan the second scan area on the scanning object.

According to another aspect of the present disclosure, a method is provided. The method may be implemented on at least one machine each of which has at least one processor and a storage device. The method may include determining, by the at least one processor, a first scan area on a scanning object. The method may also include acquiring, by the at least one processor, raw data generated by scanning the first scan area on the scanning object and generating, by the at least one processor, a positioning image based on the raw data. The method may also include generating, by the at least one processor, a pixel value distribution curve based on the positioning image and determining, by the at least one processor, a second scan area on the scanning object based on the pixel value distribution curve. The method may further include causing, by the at least one processor, a scanner to scan the second scan area on the scanning object.

According to yet another aspect of the present disclosure, a non-transitory computer-readable storage medium is provided. The non-transitory computer-readable storage medium may include a set of instructions. When the set of instructions is executed by a computing device including at least one processor, the set of instructions may cause the computing device to implement a method. The method may include determining, by the at least one processor, a first scan area on a scanning object. The method may also include acquiring, by the at least one processor, raw data generated by scanning the first scan area on the scanning object and generating, by the at least one processor, a positioning image based on the raw data. The method may also include generating, by the at least one processor, a pixel value distribution curve based on the positioning image and determining, by the at least one processor, a second scan area on the scanning object based on the pixel value distribution curve. The method may further include causing, by the at least one processor, a scanner to scan the second scan area on the scanning object.

In some embodiments, the at least one processor may be configured to cause the system further to determine a sum of pixel values of the positioning image along a direction and generate the pixel value distribution curve.

In some embodiments, the direction includes a direction perpendicular to a long axis direction of the scanning object.

In some embodiments, the at least one processor may be configured to cause the system further to determine a pixel value distribution histogram of the positioning image and determine, based on the pixel value distribution histogram, a background pixel value. The at least one processor may be configured to cause the system further to determine a reduced image by subtracting the background pixel value from the positioning image and determine a sum of pixel values of the reduced image along a direction. The at least one processor may be configured to cause the system further to generate, based on the sum of pixel values, the pixel value distribution curve.

In some embodiments, the background pixel value includes a pixel value of a peak in the pixel value distribution histogram.

In some embodiments, the at least one processor may be configured to cause the system further to determine a binary image based on the positioning image and determine a sum of pixel values of the binary image along a direction. The at least one processor may be configured to cause the system further to generate, based on the sum of pixel values, the pixel value distribution curve.

In some embodiments, the at least one processor may be configured to cause the system further to compare each pixel value of the positioning image with a predetermined value, and generate the binary image by modifying the pixels of the positioning image having pixel value below the predetermined value to 0, and modifying the pixels of the positioning image having pixel value equals or exceeds the predetermined value to 1.

In some embodiments, the predetermined value includes a background pixel value of the positioning image.

In some embodiments, the at least one processor may be configured to cause the system further to determine curvatures of a plurality of points in the pixel value distribution curve, and determine one or more points from the plurality of points in the pixel value distribution curve that have curvatures greater than a threshold curvature. The at least one processor may be configured to cause the system further to determine the second scan area based on the one or more points.

In some embodiments, the at least one processor may be configured to cause the system further to determine a first boundary and a second boundary of the second scan area based on the one or more points.

In some embodiments, the second scan area includes one or more sub-scan areas, and the at least one processor may be configured to cause the system further to determine a first boundary and a second boundary of each of the one or more sub-scan areas based on the one or more points.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 1-A is schematic diagrams illustrating an exemplary imaging system according to some embodiments of the present disclosure;

FIG. 1-B is schematic diagrams illustrating an exemplary scan module according to some embodiments of the present disclosure.

FIG. 5 is a block diagram illustrating an exemplary processing module according to some embodiments of the present disclosure;

FIG. 10 is a block diagram illustrating an exemplary second scan area determination unit according to some embodiments of the present disclosure;

DETAILED DESCRIPTION

Figure 2:
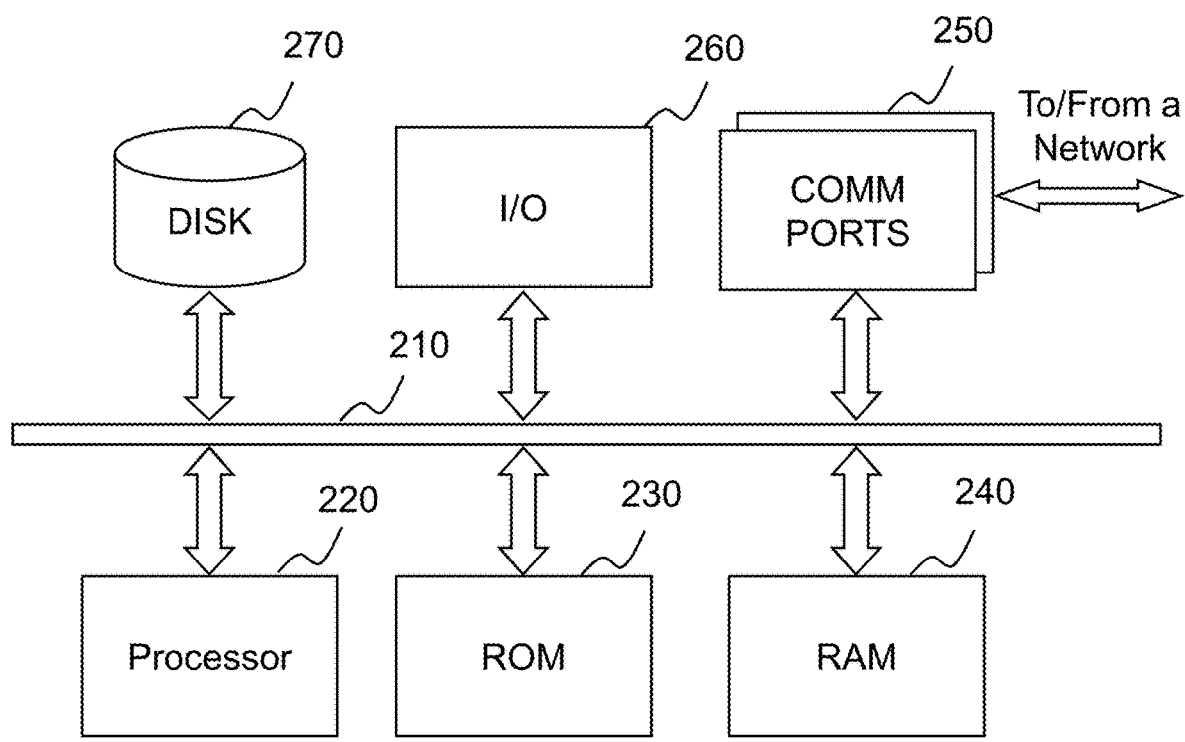
FIG. 2 is a schematic diagram illustrating hardware and/or software components of an exemplary computing device according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Generally, the word "module," "unit," "sub-unit," or "block," as used herein, refers to logic embodied in hardware or firmware, or to a collection of software instructions. A module, a unit, a sub-unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 220 illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, sub-unit, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for illustration and description only and are not intended to limit the scope of the present disclosure. It is understood that the drawings are not to scale.

Provided herein are systems and components for non-invasive imaging, such as for disease diagnostic or research purposes. The imaging system may find its applications in different fields such as medicine or industry. For example, the imaging system may be used in internal inspection of components including, for example, flaw detection, security scanning, failure analysis, metrology, assembly analysis, void analysis, wall thickness analysis, or the like, or any combination thereof.

The present disclosure describes system and method for determining a scan area based on a positioning image. For example, the system may perform the method to determine a first scan area on a scanning object, and acquire raw data generated by scanning the first scan area on the scanning object to reconstruct a positioning image based on the raw data. The system may also perform the method to generate a pixel value distribution curve of the positioning image. The system may further perform the method to determine a second scan area on the scanning object based on the pixel value distribution curve. In some embodiments, the system may perform the method to scan the second scan area on the scanning object.

FIG. 1-A is schematic diagrams illustrating an exemplary imaging system according to some embodiments of the present disclosure. The imaging system 100 may include a Computed Tomography (CT) system, an Emission Computed Tomography (ECT) system (e.g., a Positron Emission Tomography (PET) system, a Single Photon Emission Computed Tomography (SPECT) system), and a multi-modality system, a Magnetic Resonance Imaging (MRI) system, etc. The imaging system 100 may include a multi-modality system including, for example, a Computed Tomography-Positron Emission Tomography (CT-PET) system, a Magnetic Resonance-Positron Emission Tomography (MR-PET) system, etc. In some embodiments, the imaging system 100 may include modules and/or components for performing CT imaging and/or related analysis. Merely by way of example, the imaging system 100 may include a scanner 110, a network 120, a storage device 130, a host computer 140, and one or more terminals 150.

In some embodiments, the scanner 110, the host computer 140, the terminals 150, and the storage device 130 may be connected to and/or communicate with each other via a wireless connection (e.g., the network 120), a wired connection, or a combination thereof. The connection between the components of the imaging system 100 may be variable. Merely by way of example, the scanner 110 may be connected to the host computer 140 through the network 120, as illustrated in FIG. 1. As another example, the scanner 110 may be connected to the host computer 140 directly. As a further example, the storage device 130 may be connected to the host computer 140 through the network 120, as illustrated in FIG. 1, or connected to the host computer 140 directly.

The scanner 110 may be configured to scan an object (not shown in FIG. 1) under examination and generate raw data of the object. The object may include a substance, a tissue, an organ, a specimen, a body, or the like, or any combination thereof. In some embodiments, the object may include a patient or a part thereof. The object may include a head, a breast, a lung, a pleura, a mediastinum, an abdomen, a long intestine, a small intestine, a bladder, a gallbladder, a triple warmer, a pelvic cavity, a backbone, extremities, a skeleton, a blood vessel, or the like, or any combination thereof. The scanner 110 may include a gantry 111, a scan module 112 mounted on the gantry 111, a detection region 113, and a subject table 114.

The network 120 may include any suitable network that can facilitate the exchange of information and/or data within the imaging system 100 or between a component of the imaging system 100 and an external device. In some embodiments, one or more components of the imaging system 100 (e.g., the scanner 110, the storage device 130, the host computer 140, the terminals 150) may exchange information and/or data with one or more other components of the imaging system 100 via the network 120. For example, the host computer 140 may receive raw data from the scanner 110 or the storage device 130 directly or via the network 120.

The network 120 may be a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LTE) network), a frame relay network, a virtual private network (VPN), a satellite network, a telephone network, routers, hubs, switches, server computers, or the like, or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The storage device 130 may store data, instructions, and/or any other information. In some embodiments, the storage device 130 may store raw data obtained by the scanner 110. In some embodiments, the storage device 130 may store data obtained from the host computer 140. In some embodiments, the storage device 130 may store data and/or instructions that the host computer 140 may execute or use to perform exemplary processes or methods described in the present disclosure.

In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 120 to communicate with one or more other components of the imaging system 100 (e.g., the scanner 110, the host computer 140, the terminals 150). One or more components of the imaging system 100 may access the data or instructions stored in the storage device 130 via the network 120. In some embodiments, the storage device 130 may be directly connected to or communicate with one or more other components of the imaging system 100 (e.g., the scanner 110, the host computer 140, the terminals 150). In some embodiments, the storage device 130 may be part of the host computer 140.

The host computer 140 may process data (e.g., raw data, a plurality of image slices) obtained from the scanner 110, and/or the storage device 130. In some embodiments, the host computer 140 may be a single server or a server group. The server group may be centralized or distributed. In some embodiments, the host computer 140 may be local to or remote from other components of the imaging system 100. The host computer 140 may access raw data produced by the scanner 110, stored by the storage device 130, an external storage device via, for example, the network 120. Alternatively, the host computer 140 may be directly connected to the scanner 110, and/or the storage device 130 to access the raw data. In some embodiments, the host computer 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the host computer 140 may be implemented by a computing device 200 having one or more components illustrated in FIG. 2.

In some embodiments, the host computer 140 may include a console, a user (e.g., doctor or imaging engineer) may control the scanner 110 to scan an object (e.g., patient) via the console. The description of the host computer 140 may be found elsewhere in the disclosure.

The terminal(s) 150 may include a mobile device 151, a tablet computer 152, a laptop computer 153, etc. In some embodiments, the mobile device 151 may include a smart home device, a wearable device, a mobile device, a virtual reality device, an augmented reality device, or the like, or any combination thereof. Exemplary smart home device may include a smart lighting device, a control device of an intelligent electrical apparatus, a smart monitoring device, a smart television, a smart video camera, an interphone, or the like, or any combination thereof. Exemplary wearable device may include a bracelet, footgear, eyeglasses, a helmet, a watch, clothing, a backpack, a smart accessory, or the like, or any combination thereof. Exemplary mobile device may include a mobile phone, a personal digital assistant (PDA), a gaming device, a navigation device, a point of sale (POS) device, a laptop, a tablet computer, a desktop, or the like, or any combination thereof. Exemplary virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 150 may be implemented on the host computer 140.

It should be noted that the above description of the imaging system 100 is merely provided for illustration, and not intended to limit the scope of the present disclosure. For persons having ordinary skills in the art, multiple variations and modifications may be made under the teachings of the present disclosure. For example, the assembly and/or function of the imaging system 100 may be varied or changed according to specific implementation scenarios. Merely by way of example, some other components may be added into the imaging system 100, such as a patient positioning unit, a gradient amplifier unit, and other devices or units. However, those variations and modifications do not depart from the scope of the present disclosure.

FIG. 1-B is schematic diagrams illustrating an exemplary scan module according to some embodiments of the present disclosure. As shown in FIG. 2, the scan module 112 may be a multi-modality module which includes a PET scanning unit 121 and a CT scanning unit 122. The PET scanning unit 121 may include one or more PET scanning sub-units, such as PET scanning sub-unit 1, PET scanning sub-unit 2, . . . PET scanning sub-unit n. In some embodiments, the one or more PET scanning sub-units may be independent each other or at least partly related. The PET scanning sub-unit may perform PET scan to the object and obtain PET data. The scan module 112 may also be a CT scan module or a PET scan module.

The CT scanning unit 122 may include X-ray generator and X-ray detector. The X-ray generator may include one or more X-ray tubes. An X-ray tube may emit X-rays (or referred to as X-ray beams). The X-ray generator may be a cold cathode ion tube, a high vacuum hot cathode tube, a rotating anode tube, etc. The shape of the emitted X-ray beams may be a line, a narrow pencil, a narrow fan, a fan, a cone, a wedge, or the like, or an irregular shape, or any combination thereof. An X-ray tube in the X-ray generator may be fixed at a location. An X-ray tube may be translated or rotated in some scenarios.

The X-ray detector may be configured to receive the X-rays emitted from the X-ray generator or other radiation source, and generate the raw data of an X-ray image of the object under examination. The X-rays from the X-ray generator may traverse the object under examination, and then reach the X-ray detector. After receiving the X-rays, the X-ray detector may generate raw data of an X-ray image of the object under examination. The term "raw data" may refer to data that may be detected by the X-ray detector, and the raw data may be utilized to reconstruct an X-ray image. The shape of the X-ray detector may be flat, arc-shaped, circular, or the like, or any combination thereof. The fan angle of the arc-shaped detector may be an angle ranging from 0° to 360°. The fan angle may be fixed or adjustable according to different conditions including, for example, the desired resolution of an image, the size of an image, the sensitivity of a detector, the stability of a detector, or the like, or any combination thereof. In some embodiments, the pixels of the X-ray detector may be the number of the smallest detecting units, e.g., the number of detector cells (e.g., a scintillator or a photosensor). The pixels of the X-ray detector may be arranged in a single row, two rows, or another number of rows. The X-ray detector may be one-dimensional, two-dimensional, or three-dimensional.

In some embodiments, the raw data may be stored or archived in a storage (e.g., the storage device 130 or a storage module of the host computer 140), processed by the host computer 140, or transferred to an external processing and/or storage device (e.g., a cloud server) via a cable, or a wired or wireless network (e.g., the network 120).

FIG. 2 is a schematic diagram illustrating hardware and/or software components of an exemplary computing device on which the host computer 140 may be implemented according to some embodiments of the present disclosure. For example, the host computer 140 may be implemented on the computing device 200 and configured to perform functions of the host computer 140 disclosed in this disclosure.

The computing device 200 may be a general purpose computer or a special purpose computer. Both may be used to implement the host computer 140 of the present disclosure. For example, the host computer 140 of the imaging system 100 may be implemented on the computing device 200, via its hardware, software program, firmware, or a combination thereof. Although only one such computer is shown for convenience, the computer functions related to the imaging system 100 as described herein may be implemented in a distributed manner on a number of similar platforms to distribute the processing load.

The computing device 200, for example, may include communication (COMM) ports 250 connected to and from a network (e.g., the network 120) connected thereto to facilitate data communications. The computing device 200 may also include a processor (e.g., a central processing unit (CPU)) 220, in the form of one or more processors (e.g., logic circuits), for executing program instructions. For example, the processor 220 may include interface circuits and processing circuits therein. The interface circuits may be configured to receive electronic signals from a bus 210, wherein the electronic signals encode structured data and/or instructions for the processing circuits to process. The processing circuits may conduct logic calculations, and then determine a conclusion, a result, and/or an instruction encoded as electronic signals. Then the interface circuits may send out the electronic signals from the processing circuits via the bus 210.

The computer device 200 may include program storage and data storage of different forms, for example, a disk 270, and a read only memory (ROM) 230, or a random access memory (RAM) 240, for various data files to be processed and/or transmitted by the computer. The computing device 200 may also include program instructions stored in the ROM 230, the RAM 240, and/or other type of non-transitory storage medium to be executed by the processor 220. The methods and/or processes of the present disclosure may be implemented as the program instructions. The computing device 200 also includes an I/O component 260, supporting input/output between the computer and other components therein. The computing device 200 may also receive programming and data via network communications.

Merely for illustration purposes, only one processor is described in the computing device 200. However, it should be noted that the computing device 200 in the present disclosure may also include multiple processors. Thus operations that are performed by one processor as described in the present disclosure may also be jointly or separately performed by the multiple processors. For example, the processor of the computing device 200 executes both operation A and operation B. As another example, operation A and operation B may also be performed by two different processors jointly or separately in the computing device 200 (e.g., the first processor executes operation A and the second processor executes operation B, or the first and second processors jointly execute operations A and B).

Figure 3:
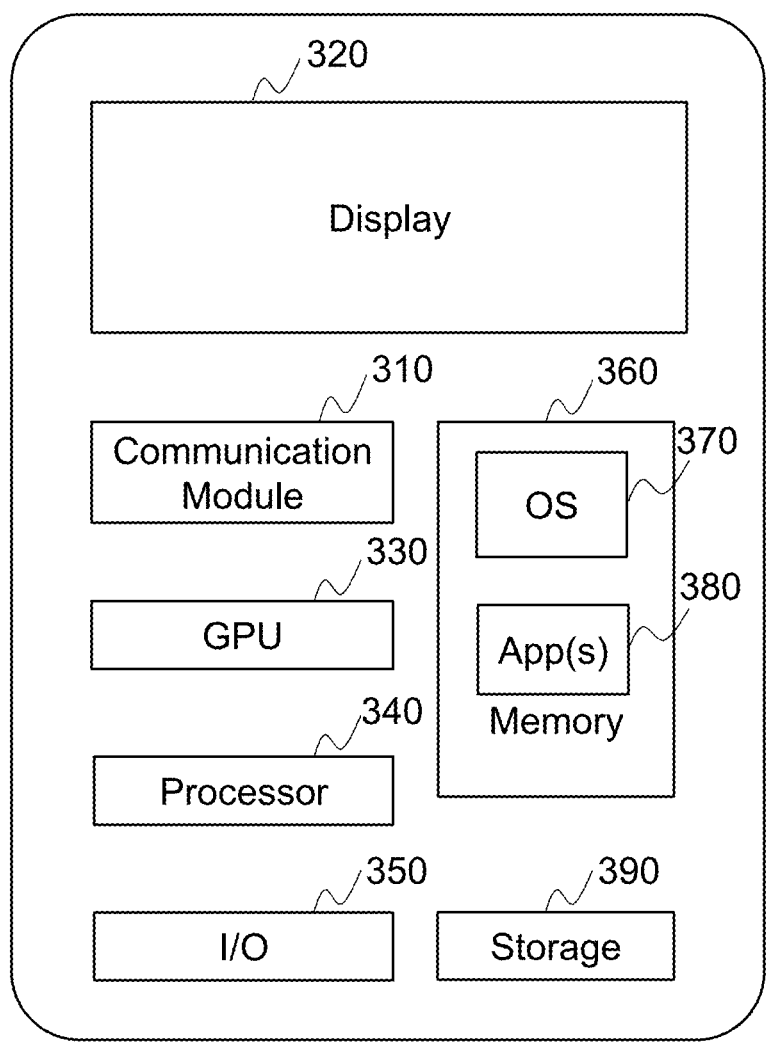
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device on which the terminals 150 may be implemented according to some embodiments of the present disclosure. As illustrated in FIG. 3, the mobile device 300 may include a communication module 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 to be executed by the CPU 340. The applications 380 may include a browser or any other suitable mobile apps for receiving and rendering information relating to image processing or other information from the host computer 140. User interactions with the information stream may be achieved via the I/O 350 and provided to the host computer 140 and/or other components of the imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
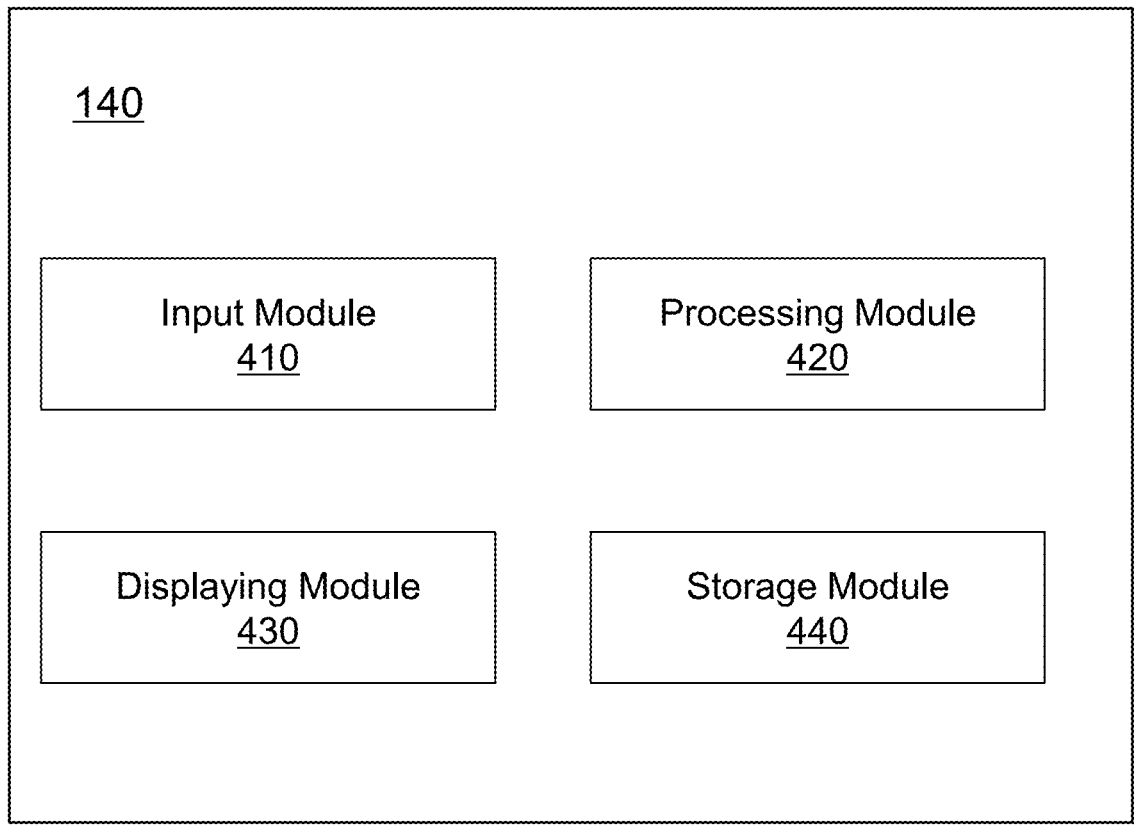
FIG. 4 is a block diagram illustrating an exemplary host computer according to some embodiments of the present disclosure.

FIG. 4 is a block diagram illustrating an exemplary host computer according to some embodiments of the present disclosure. As illustrated in FIG. 4, the host computer 140 may include an input module 410, a processing module 420, a displaying module 430, and a storage module 440.

The input module 410 may be configured to receive information input by a user. In some embodiments, the information received by the input module 410 may be stored in the storage module 440, and/or be transmitted to the processing module 420 for further processing. In some embodiments, the information received by the input module 410 may include controlling instructions, and may be transmitted to the scanner 110 and/or the scan module 112 to set scan parameters and/or perform a scanning. For example, the input module 410 may be configured to receive a scan area of a positioning scanning and/or an imaging scanning.

The processing module 420 may be configured to process data. In some embodiments, the processing module 420 may obtain data from the scanner 110, the input module 410, or the storage module 440. The processing module 420 may process data using one or more processing operations. In some embodiments, the one or more processing operations may include but not limited to fitting, interpolation, discrete, analog-to-digital conversion, superposition, Fourier transform, filtering, projection, denoising, feature extraction, image reconstruction, and image enhancement, etc. For example, the processing module 420 may obtain raw data from the scanner 110, such as the CT scanning unit 122, and reconstruct a positioning image based on the raw data. Alternatively or additionally, the processing module 420 may further process the reconstructed positioning image using at least one operation of reducing by background value, filtering and noise reduction, converting a positioning image to a binary image, or projection and accumulation.

The displaying module 430 may be configured to display information. The information may include output of the processing module 420, such as a positioning image or the like. In some embodiments, the information may also include instructions using to prompt user to perform an input or other control operations.

The storage module 440 may be configured to store information and/or data received from the input module 410, raw data generated by the scanner 110, processed data by the processing module 420, reconstructed image, or the like, or any combination thereof. In some embodiments, the storage module 440 may include a mass storage, removable storage, a volatile read-and-write memory, a read-only memory (ROM), or the like, or any combination thereof. The mass storage may include a magnetic disk, an optical disk, a solid-state drive, etc. The removable storage may include a flash drive, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage module 440 may store one or more programs and/or instructions that may be executed by the processor 220 of the host computer 140 (e.g., the processing module 420) to perform exemplary methods and/or processes described in the disclosure. For example, the storage module 440 may store programs and/or instructions executed by the processor 220 of the host computer 140 to obtain raw data, reconstruct a positioning image based on the raw data, process the positioning image, determine a scan area on the positioning image, cause the scanner 110 to scan the scan area, or display any information or image.

The modules of the host computer 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined into a single module, and any one of the modules may be divided into two or more units. For example, the input module 410 and the displaying module 430 may be combined into a single module (e.g., a touch screen) that may be configured to receive information and/or data input by a user, and display a positioning image or other information.

FIG. 5 is a block diagram illustrating an exemplary processing module according to some embodiments of the present disclosure. As illustrated in FIG. 5, the processing module 420 may include a first scan area determination unit 502, an acquisition unit 504, a reconstruction unit 506, a distribution curve generation unit 508, a second scan area determination unit 510, and a control unit 512.

The first scan area determination unit 502 may be configured to determine a first scan area of an object under examination. In some embodiments, the first scan area determination unit 502 may determine the first scan area of the object according to an input of a user through the input module 410. For example, after the object lying on the subject table 114, the user may input and/or select a region of the subject table 114, and the first scan area determination unit 502 may determine the overlay part of the object with the input region as the first scan area. In some embodiments, the object under examination may include a patient and the first scan area of the object may include head, torso, abdomen, chest, whole body, etc.

The acquisition unit 504 may be configured to acquire raw data from the scanner 110 and/or the storage device 130. In some embodiments, the raw data may be generated by the scanner scanning the first scan area of the object. For example, the scanner 110 may perform a positioning scan to the first scan area of the object determined by the first scan area determination unit 502, and generate raw data of the object under examination. Merely by way of example, the scanner 110 may include a scan module 112, the scan module 112 may be a multi-modality scan module which including PET scanning unit 121 and CT scanning unit 122. In some embodiments, the scanner 110 may perform the positioning scan using the CT scanning unit 122. In the positioning scan, the X-ray generator may be fixed in a specific position and the subject table 114 may move. Alternatively or additionally, the scanner 110 may perform the positioning scan using the PET scanning unit 121. The raw data may be generated after the positioning scan to the first scan area of the object.

The reconstruction unit 506 may be configured to generate an image. In some embodiments, the reconstruction unit 506 may obtain raw data acquired by the acquisition unit 504, and reconstruct the raw data to generate a positioning image. In some embodiments, the reconstruction unit 506 may transmit the reconstructed positioning image to the storage module 440 and/or the displaying module 430. The positioning image may be used to determine a second scan area of the object in order to perform an imaging scan.

Figure 16:
FIG. 16 is a graph illustrating an exemplary positioning image according to some embodiments of the present disclosure.

Merely by way of example, the first scan area may include head and torso of a patient, and the scanner 110 may perform a positioning scan to the head and torso to generate the raw data. The reconstruction unit 506 may reconstruct a positioning image based on the raw data, as shown in FIG. 16.

The distribution curve generation unit 508 may be configured to generate a pixel value distribution curve based on an image. In some embodiments, the pixel value distribution curve may represent a sum of pixel values of an image along a first direction as a function of a position along a second direction, wherein the first direction being perpendicular to the second direction. For example, the distribution curve generation unit 508 may determine a sum by accumulating values of pixels in different columns of the positioning image shown in FIG. 16 along the X direction (i.e., for each row), and generate the pixel value distribution curve, as described elsewhere in the present disclosure. Alternatively or additionally, the distribution curve generation unit 508 may reduce all pixels in the positioning image by a background pixel value to generate a reduced image, and generate a pixel value distribution curve of the reduced image.

In some embodiments, the distribution curve generation unit 508 may convert the positioning image into a binary image, and generate a pixel value distribution curve of the binary image. Details of the distribution curve generation unit 508 may be described elsewhere in the present disclosure, such as FIG. 7 and the description thereof.

The second scan area determination unit 510 may be configured to determine a second scan area on a positioning image of an object based on a pixel value distribution curve of the positioning image. In some embodiments, the second scan area determination unit 510 may determine curvatures of a plurality of points of the pixel value distribution curve, and determine one or more points from the plurality of points, wherein the curvatures of the one or more points exceeding a threshold curvature. The second scan area determination unit 510 may determine the second scan area based on the one or more points. Details of the second scan area determination unit 510 may be described elsewhere in the present disclosure, e.g., FIG. 10 and the description thereof.

The control unit 512 may be configured to generate a controlling instruction to cause the scanner 110 scanning the second scan area of an object determined by the second scan area determination unit 510. For example, the control unit 512 may obtain the second scan area on the positioning image, and generate controlling instruction based on the second scan area. The scanner 110 may move the subject table 114 and cause the scan module 112 to scan the second scan area of the object according the controlling instruction.

The units of the processing module 420 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the units may be combined into a single unit, and any one of the units may be divided into two or more units. For example, the acquisition unit 504 and the reconstruction unit 506 may be combined into a single unit that may be configured to obtain the raw data and reconstruct a positioning image based on the obtained raw data.

Figure 6:
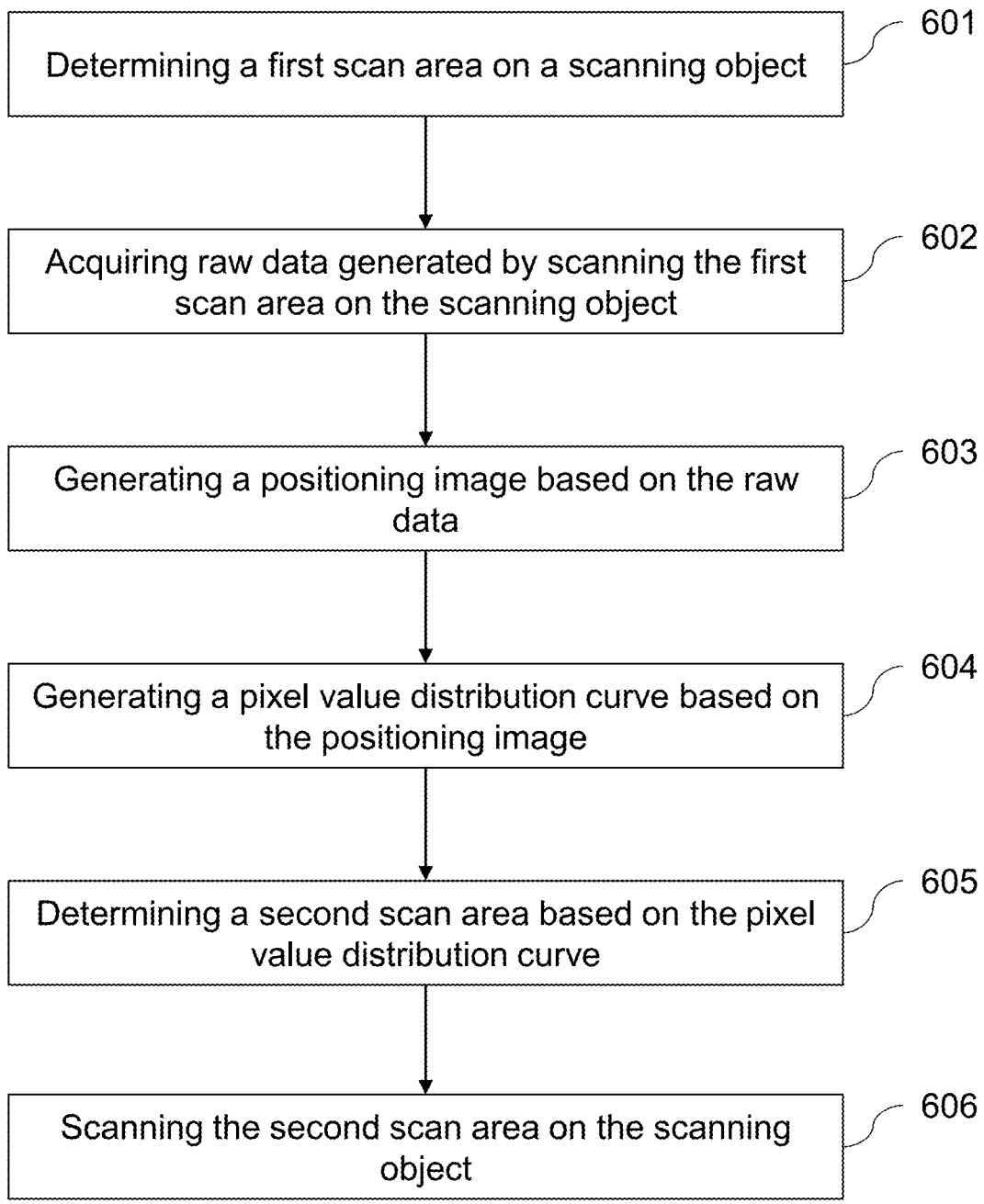
FIG. 6 is a flowchart illustrating an exemplary process of scanning a second scan area according to some embodiments of the present disclosure.

FIG. 6 is a flowchart illustrating an exemplary process of scanning a second scan area according to some embodiments of the present disclosure. The process 600 may be executed by the host computer 140. For example, the process 600 may be implemented as a set of instructions stored in the ROM 230 or the RAM 240. The processor 220 and/or the units 502-512 illustrated in FIG. 5 may execute the set of instructions, and when executing the instructions, the processor 220 and/or the units 502-512 may be configured to perform the process 600. The operations of the process 600 presented below are intended to be illustrative. In some embodiments, the process 600 may be accomplished with one or more additional operations not described and/or without one or more of the operations discussed. The order in which the operations of the process 600 illustrated in FIG. 6 and described below is not intended to be limiting.

In 601, the host computer 140 (e.g., the first scan area determination unit 502, the interface circuits of the processor 220) may determine a first scan area of an object under examination. In some embodiments, the host computer 140 may receive an input of a user through the input module 410, and determine the first scan area of the object according to the input of the user. For example, after the object lying on the subject table 114, the user may input and/or select a region on the subject table 114, and the host computer 140 may determine the overlay part of the object with the input region as the first scan area. In some embodiments, the object under examination may include a patient and the first scan area of the object may include head, torso, abdomen, chest, whole body, etc.

In 602, the host computer 140 (e.g., the acquisition unit 504, the interface circuits of the processor 220) may acquire raw data of an object from the scanner 110 and/or the storage device 130. In some embodiments, the raw data may be generated by the scanner 110 scanning the first scan area of the object. For example, the host computer 140 may generate a controlling instruction, which may cause the scanner 110 to perform a positioning scan to the first scan area of the object, and generate raw data of the object under examination. The first scan area of the object may be determined by the first scan area determination unit 502. Merely by way of example, the scanner 110 may include a scan module 112 which including PET scanning unit 121 and CT scanning unit 122. In some embodiments, the scanner 110 may perform the positioning scan using the CT scanning unit 122. In the positioning scan, the X-ray generator may be fixed in a specific position (e.g., the gantry 111 is fixed) and the subject table 114 may move. Alternatively or additionally, the scanner 110 may perform the positioning scan using the PET scanning unit 121. The raw data may be generated after the positioning scan to the first scan area of the object.

The raw data may be transmitted to a storage (e.g., the storage device 130 and/or the storage module 440).

In 603, the host computer 140 (e.g., the reconstruction unit 506, the processing circuits of the processor 220) may generate an image. In some embodiments, the host computer 140 may obtain raw data acquired by the acquisition unit 504, and reconstruct the raw data to generate a positioning image. In some embodiments, the host computer 140 may transmit the reconstructed positioning image to the storage module 440 and/or the displaying module 430.

For example, in 602, the host computer 140 may acquire the raw data generated by the scanner 110 by scanning head and torso of a patient, and in 603, the host computer 140 may generate a positioning image of head and torso of the patient, as illustrated in FIG. 16. The positioning image shown in FIG. 16 is an image of coronal plane of the first scan area. The Z direction is the long axis direction of the scanning object, e.g., the patient. Merely by way of example, the positioning image shown in FIG. 16 may be used to determine a second scan area of the scanning object, as described elsewhere in the present disclosure. Alternatively or additionally, the positioning image may be an image of sagittal plane.

Figure 13:
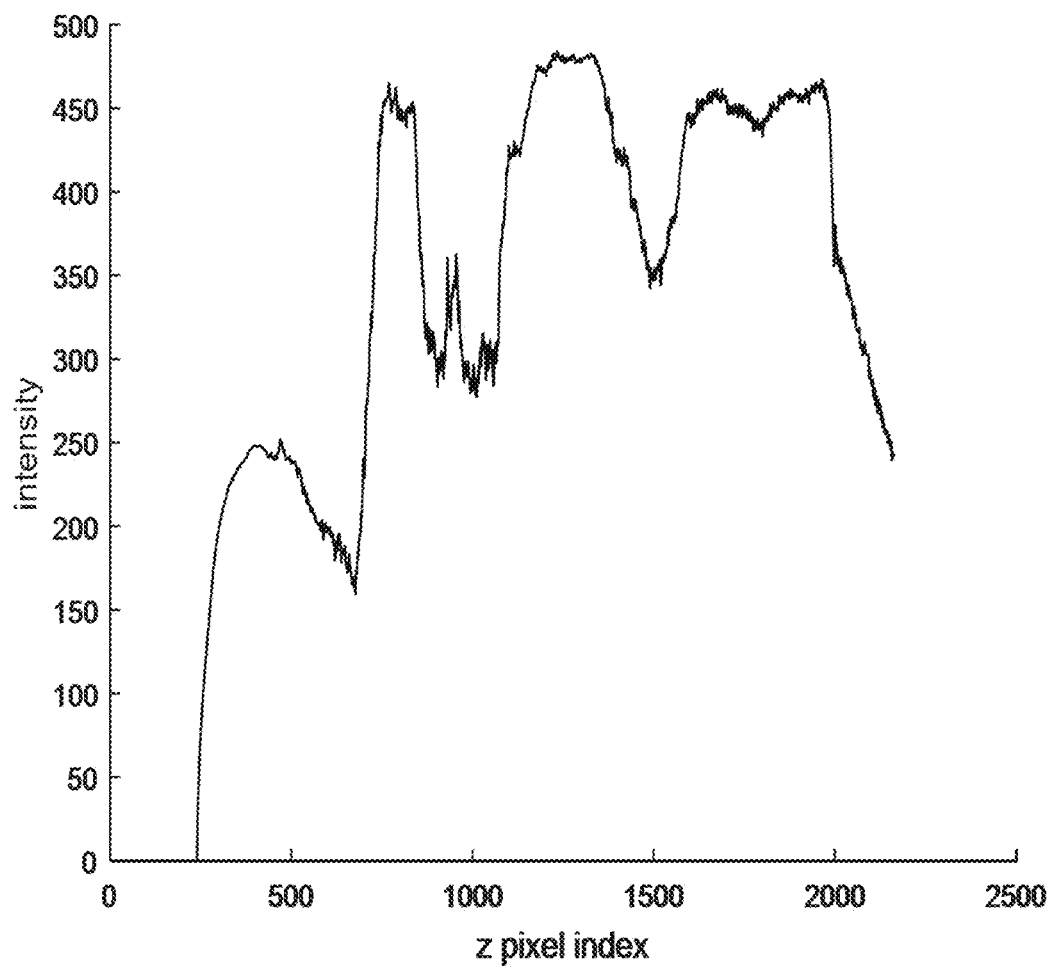
FIG. 13 is a graph illustrating an exemplary pixel value distribution curve according to some embodiments of the present disclosure.

In 604, the host computer 140 (e.g., the distribution curve generation unit 508, the processing circuits of the processor 220) may generate a pixel value distribution curve based on the positioning image generated by the reconstruction unit 506. In some embodiments, the host computer 140 may determine a sum by accumulating values of pixels in different columns of the positioning image shown in FIG. 16 along the X direction (i.e., for each row), and generate the pixel value distribution curve, as described elsewhere in the present disclosure. Referring to FIG. 13, which illustrating an exemplary pixel value distribution curve, the horizontal axis represents "Z pixel index," e.g., the row count along Z direction of the positioning image shown in FIG. 16, and the vertical axis represents "intensity," e.g., the sum of pixels in different columns of the same row. Alternatively or additionally, the host computer 140 may reduce all pixels in the positioning image by a background pixel value to generate a reduced image, and generate a pixel value distribution curve of the reduced image.

In some embodiments, the host computer 140 may convert the positioning image into a binary image, and generate a pixel value distribution curve of the binary image. Details of the generation of the pixel value distribution curve may be described elsewhere in the present disclosure, e.g., FIGS. 8 and 9, and the descriptions thereof.

In 605, the host computer 140 (e.g., the second scan area determination unit 510, the processing circuits of the processor 220) may determine a second scan area based on the pixel value distribution curve generated by the distribution curve generation unit 508. In some embodiments, the host computer 140 may obtain a plurality of points from the pixel value distribution curve, and determine curvatures of the plurality of points. The host computer 140 may compare the curvatures of the plurality of points with a threshold curvature, and determine one or more points that have curvatures greater than the threshold curvature. The host computer 140 may determine the second scan area based on the one or more points. For example, the host computer 140 may determine a first point of the one or more points as a start of the second scan area and determine a second point of the one or more points as an end of the second scan area. It should be noted that a point in the pixel value distribution curve may represent a row of the positioning image. The first point may represent a first boundary, and the second point may represent a second boundary. The host computer 140 may determine the area between the first boundary and the second boundary as the second scan area. In some embodiments, the host computer 140 may determine one or more sub-scan areas based on the one or more points, and determine the second scan area consisting of the one or more sub-scan areas. Details of the determination of the second scan area may be described elsewhere in the present disclosure, e.g., FIG. 11 and the description thereof.

In 606, the host computer 140 (e.g., the control unit 512, the interface circuits of the processor 220) may generate a controlling instruction based on the second scan area determined in 605. The host computer 140 may transmit the controlling instruction to the scanner 110 to cause the scanner 110 scanning the second scan area of an object.

It should be noted that the above description is merely provided for illustration, and not intended to limit the scope of the present disclosure. For persons having ordinary skills in the art, multiple variations and modifications may be made under the teachings of the present disclosure. However, those variations and modifications do not depart from the scope of the present disclosure. For example, one or more other optional operations (e.g., a storing operation) may be added in the process 600. In the storing operation, the host computer 140 may store information and/or data associated with the positioning image, the pixel value distribution curve and the second scan area in a storage device (e.g., the storage device 130, the storage module 440) as described elsewhere in the present disclosure.

Figure 7:
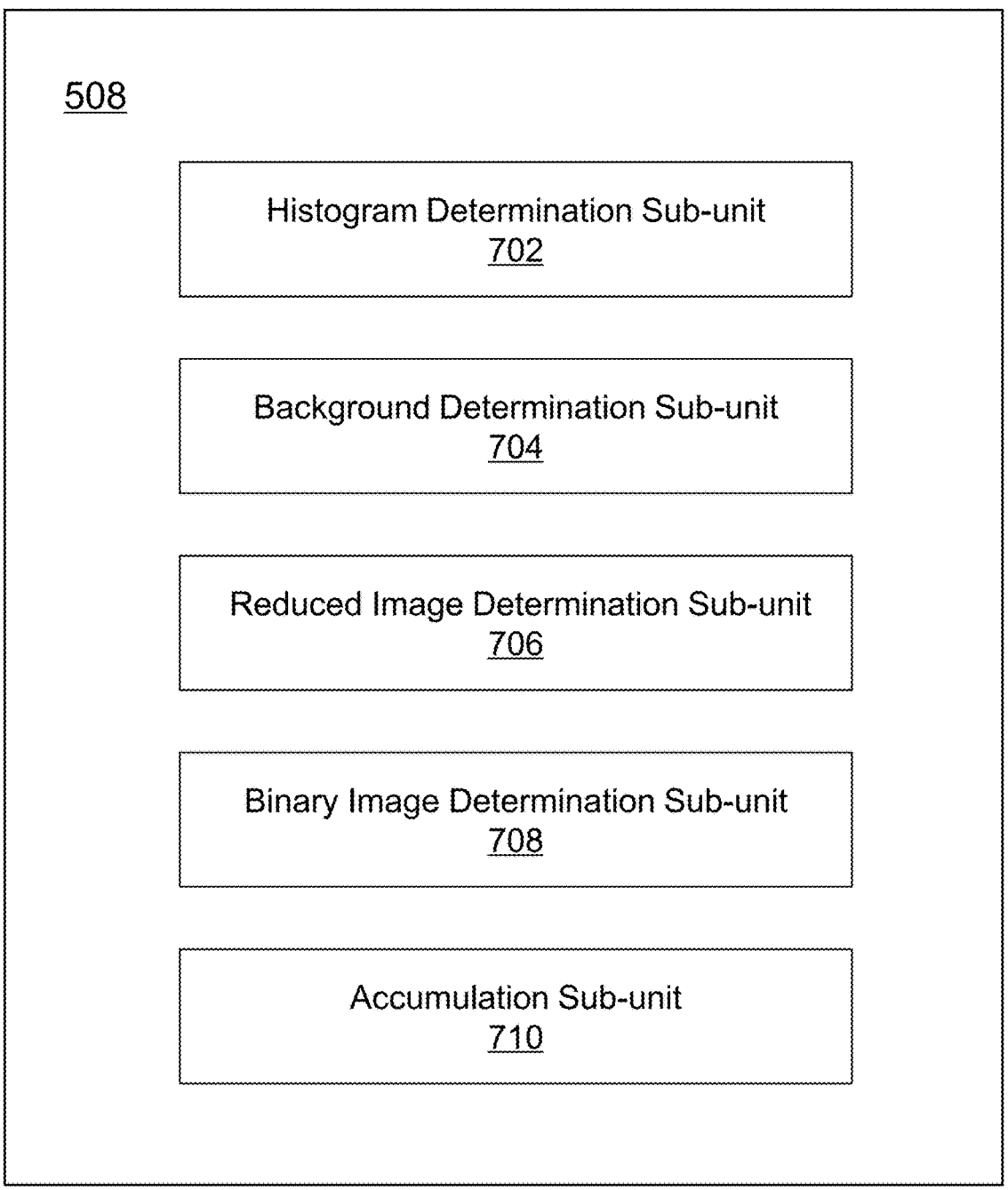
FIG. 7 is a block diagram illustrating an exemplary distribution curve generation unit according to some embodiments of the present disclosure.

FIG. 7 is a block diagram illustrating an exemplary distribution curve generation unit according to some embodiments of the present disclosure. As illustrated in FIG. 7, the distribution curve generation unit 508 may include a histogram determination sub-unit 702, a background determination sub-unit 704, a reduced image determination sub-unit 706, a binary image determination sub-unit 708, and an accumulation sub-unit 710.

The histogram determination sub-unit 702 may be configured to determine a pixel value distribution histogram of an image. In some embodiments, the histogram determination sub-unit 702 may obtain a positioning image generated by reconstruction unit 506, and determine a pixel value distribution histogram of the positioning image. As used herein, the pixel value distribution histogram may represent the pixel number as a function of pixel value. For example, the positioning image may have a plurality of pixels, and each pixel of the plurality of pixels has a pixel value. The histogram determination sub-unit 702 may count the number of pixels for each pixel value, which refers to statistics of the pixel values. The histogram determination sub-unit 702 may determine the pixel value distribution histogram according to the statistics, e.g., the pixel value and corresponding number of pixels.

The background determination sub-unit 704 may be configured to determine a background pixel value of an image. In some embodiments, the background determination sub-unit 704 may determine a background pixel value of a positioning image. For example, the background determination sub-unit 704 may obtain a pixel value distribution histogram of the positioning image determined by the histogram determination sub-unit 702, and determine the background pixel value of the positioning image based on the pixel value distribution histogram.

Alternatively or additionally, the background determination sub-unit 704 may determine the background pixel value of the positioning image based on the statistics of the pixel values of the positioning image determined by the histogram determination sub-unit 702. For example, the background determination sub-unit 704 may determine the pixel value having the most pixels as the background pixel value of the positioning image. Furthermore, the background determination sub-unit 704 may determine the background pixel value of the positioning image based on a sample database, or according to experience. For example, the sample database may include a plurality of positioning images generated previously. Each of the positioning images may have a background. The sample database may also include pixel values of the background of the each of the positioning images. The sample database may further include the average or mean value of the pixel values of the background of the each of the positioning images (which may also be referred to herein as the background pixel value of the positioning image). The sample database may also include the type(s) of each of the positioning images, such as a supine type, an obese type or a lying sideway type. The type(s) of a positioning image may relate to the background pixel value of the positioning image.

The reduced image determination sub-unit 706 may be configured to determine a reduced image of an image. In some embodiments, the reduced image determination sub-unit 706 may determine the reduced image based on the positioning image. For example, the reduced image determination sub-unit 706 may obtain the background pixel value determined by the background determination sub-unit 704, and subtract the background pixel value from the positioning image to determine the reduced image.

The binary image determination sub-unit 708 may be configured to determine a binary image based on an image. In some embodiments, the binary image determination sub-unit 708 may obtain a positioning image determined by the reconstruction unit 506, and determine a binary image of the positioning image. For example, the binary image determination sub-unit 708 may compare each pixel value of the positioning image with a predetermined value (e.g., a background pixel value determined by the background determination sub-unit 704). The binary image determination sub-unit 708 may also modify the pixel values below the predetermined value to 0 and modify the pixel values that equal or exceed the predetermined value to 1.

The accumulation sub-unit 710 may be configured to accumulate values of pixels of an image. In some embodiments, the accumulation sub-unit 710 may accumulate values of pixels along a direction, for example, along a row or a column of the image, and determine a sum of pixel values for each row or column. Furthermore, the accumulation sub-unit 710 may determine a pixel value distribution curve based on the sum of pixel values and the corresponding row count or column count.

The sub-units of the distribution curve generation unit 508 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the sub-units may be combined into a single sub-unit, and any one of the sub-units may be divided into two or more sub-units. For example, the histogram determination sub-unit 702 and the background determination sub-unit 704 may be combined into a single sub-unit that may be configured to determine a pixel value distribution histogram of an image and determine a background pixel value of the image based on the pixel value distribution histogram.

Figure 8:
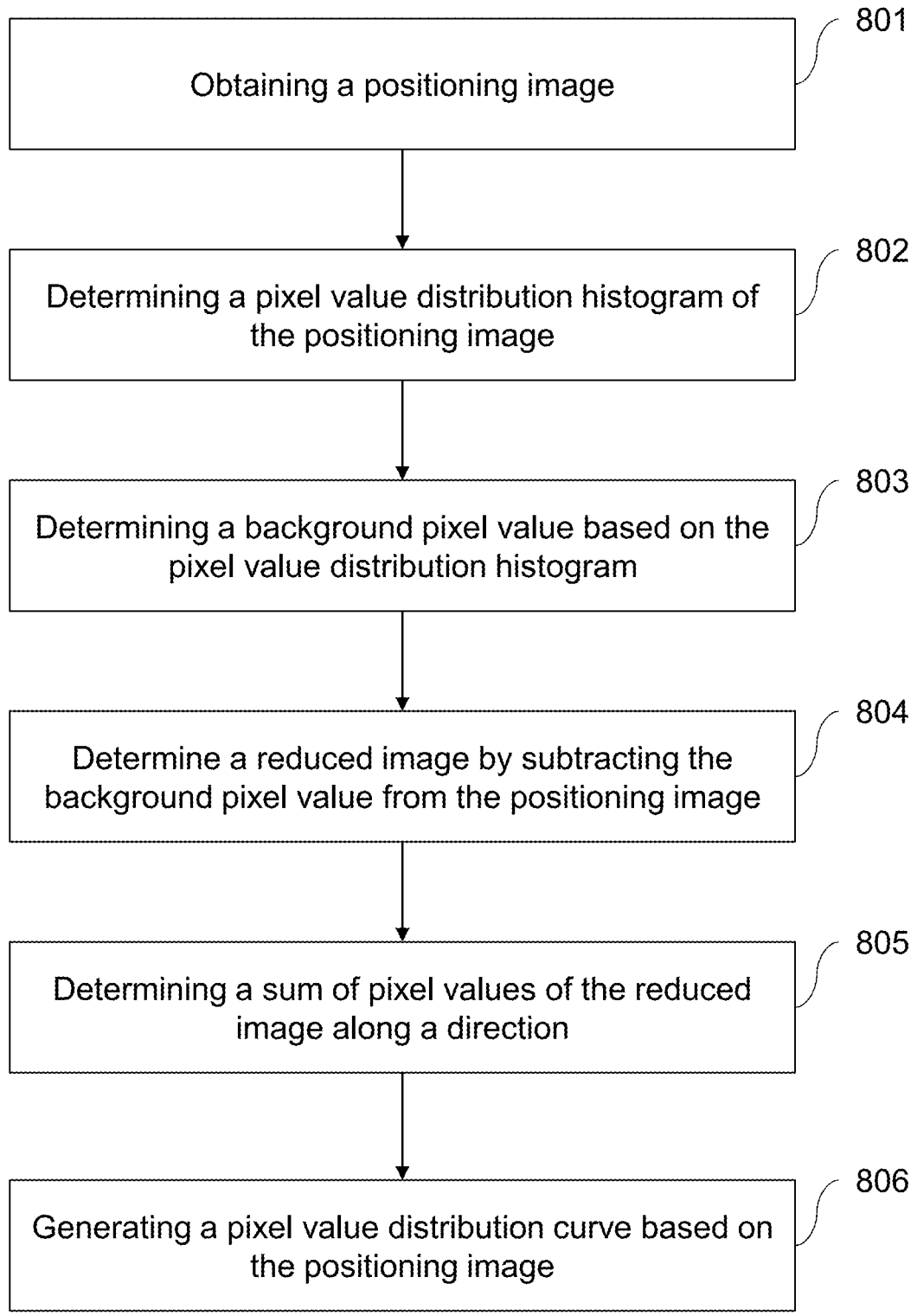
FIG. 8 is a flowchart illustrating an exemplary process of generating a pixel value distribution curve according to some embodiments of the present disclosure.

FIG. 8 is a flowchart illustrating an exemplary process of generating a pixel value distribution curve according to some embodiments of the present disclosure. The process 800 may be executed by the host computer 140. For example, the process 800 may be implemented as a set of instructions stored in the ROM 230 or the RAM 240. The processor 220 and/or the units 702-710 illustrated in FIG. 7 may execute the set of instructions, and when executing the instructions, the processor 220 and/or the units 702-710 may be configured to perform the process 800. The operations of the process 800 presented below are intended to be illustrative. In some embodiments, the process 800 may be accomplished with one or more additional operations not described and/or without one or more of the operations discussed. Additionally, the order in which the operations of the process illustrated in FIG. 8 and described below is not intended to be limiting. In some embodiments, at least part of the operation 604 of the process 600 may be performed according to the process 800.

In 801, the host computer 140 (e.g., the histogram determination sub-unit 702, the interface circuits of the processor 220) may obtain a positioning image. The positioning image may be generated by the reconstruction unit 506. In some embodiments, the host computer 140 may obtain the positioning image from the reconstruction unit 506 and/or a storage (e.g., the storage device 130, the storage module 440).

Figure 12:
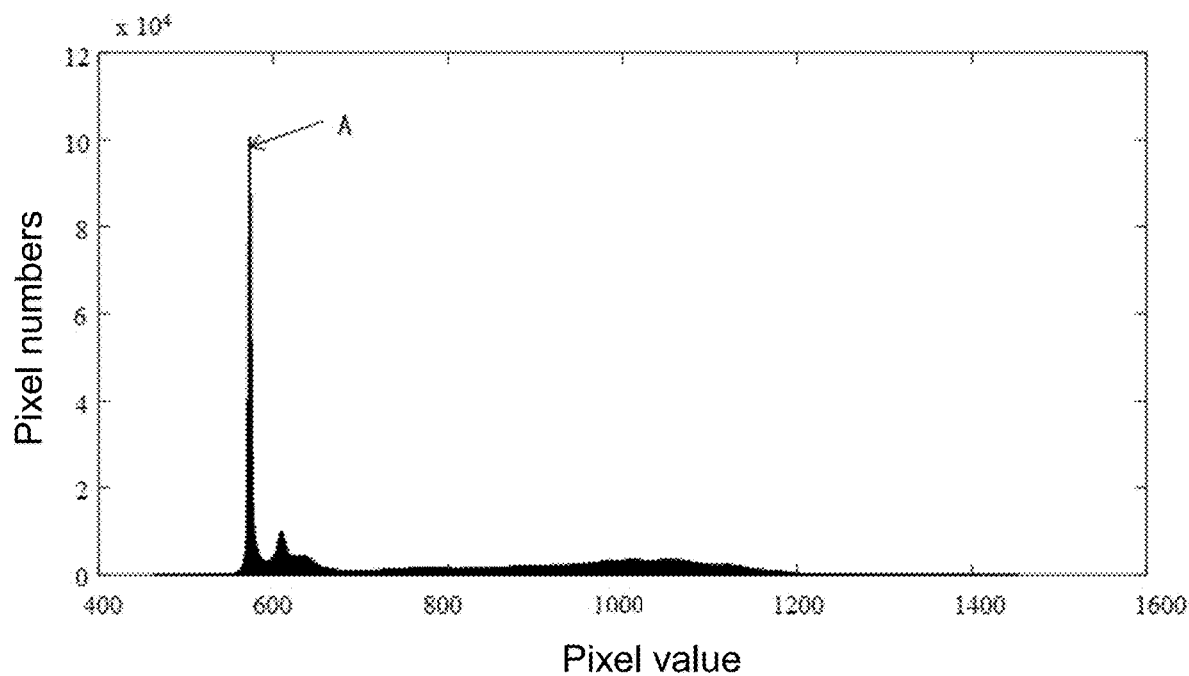
FIG. 12 is a graph illustrating an exemplary pixel value distribution histogram according to some embodiments of the present disclosure.

In 802, the host computer 140 (e.g., the histogram determination sub-unit 702, the processing circuits of the processor 220) may determine a pixel value distribution histogram of the positioning image. In some embodiments, the host computer 140 may determine statistics of the pixel values of the positioning image, and determine the pixel value distribution histogram according to the statistics. For example, the host computer 140 may count the number of pixels for each pixel values, and determine the pixel value distribution histogram. For example, FIG. 12 illustrates an exemplary pixel value distribution histogram determined by the histogram determination sub-unit 702. The horizontal axis in FIG. 12 represents the pixel value, e.g., in a range of 0-1600, and the vertical axis represents the number of pixels.

In 803, the host computer 140 (e.g., the background determination sub-unit 704, the processing circuits of the processor 220) may determine a background pixel value of the positioning image based on the pixel value distribution histogram. In some embodiments, the host computer 140 may determine the pixel value of a peak in the pixel value distribution histogram as the background pixel value. For example, as illustrated in FIG. 12, the peak A in the pixel value distribution histogram may represent that the pixel value of 590 has the most pixels (e.g., more than 100,000), and the host computer 140 may determine the pixel value 590 corresponding to the peak A as the background pixel value of the positioning image.

In 804, the host computer 140 (e.g., the reduced image determination sub-unit 706, the processing circuits of the processor 220) may determine a reduced image based on the positioning image. In some embodiments, the host computer 140 may determine the reduced image by subtracting the background pixel value determined in 803 from the positioning image.

In 805, the host computer 140 (e.g., the accumulation sub-unit 710, the processing circuits of the processor 220) may determine a sum of pixel values of the reduced image determined in 804 along a direction. In some embodiments, the direction may include the direction of the X-axis shown in FIG. 16. For example, the host computer 140 may accumulate values of the pixels along in a row of the reduced image to generate the sum of pixel values of the row. The host computer 140 may also determine a plurality of sums of the pixel values of the reduced image, and each of the plurality of sums corresponds to a row count of the reduced image (i.e., the position of a row among the rows of the reduced image).

In 806, the host computer 140 (e.g., the accumulation sub-unit 710, the processing circuits of the processor 220) may generate a pixel value distribution curve based on the positioning image. In some embodiments, the host computer 140 may generate the pixel value distribution curve of the reduced image. For example, the host computer 140 may determine a graph by determining the sums of pixel values determined in 805 as the vertical axis "intensity," and determining the row count of the binary image as the horizontal axis "Z pixel index." Each of the plurality of sums and the corresponding row count may be a point in the graph. The host computer 140 may determine a curve based on a plurality of points in the graph, which is referred to herein as a pixel value distribution curve. Refers to FIG. 13, which illustrating an exemplary pixel value distribution curve, the Z pixel index represents the row count of the reduced image, and the intensity represents the sum of pixel values of a row.

It should be noted that the above description is merely provided for illustration, and not intended to limit the scope of the present disclosure. For persons having ordinary skills in the art, multiple variations and modifications may be made under the teachings of the present disclosure. However, those variations and modifications do not depart from the scope of the present disclosure. For example, one or more other optional operations (e.g., a storing operation) may be added in the process 800. In the storing operation, the host computer 140 may store information and/or data associated with the positioning image, the pixel value distribution histogram, the background pixel value and the reduced image in a storage device (e.g., the storage device 130, the storage module 440) as described elsewhere in the present disclosure. For another example, the operation 802 may be omitted, and the host computer 140 (e.g., the background determination sub-unit 704) may determine the background pixel value directly from the positioning image, such as from the statistics of the pixel values of the positioning image. Furthermore, the operations 802, 803 and 804 may be omitted, and the host computer 140 (e.g., the accumulation sub-unit 710) may determine a sum of pixel values of the positioning image, and generate the pixel value distribution curve of the positioning image directly.

Figure 9:
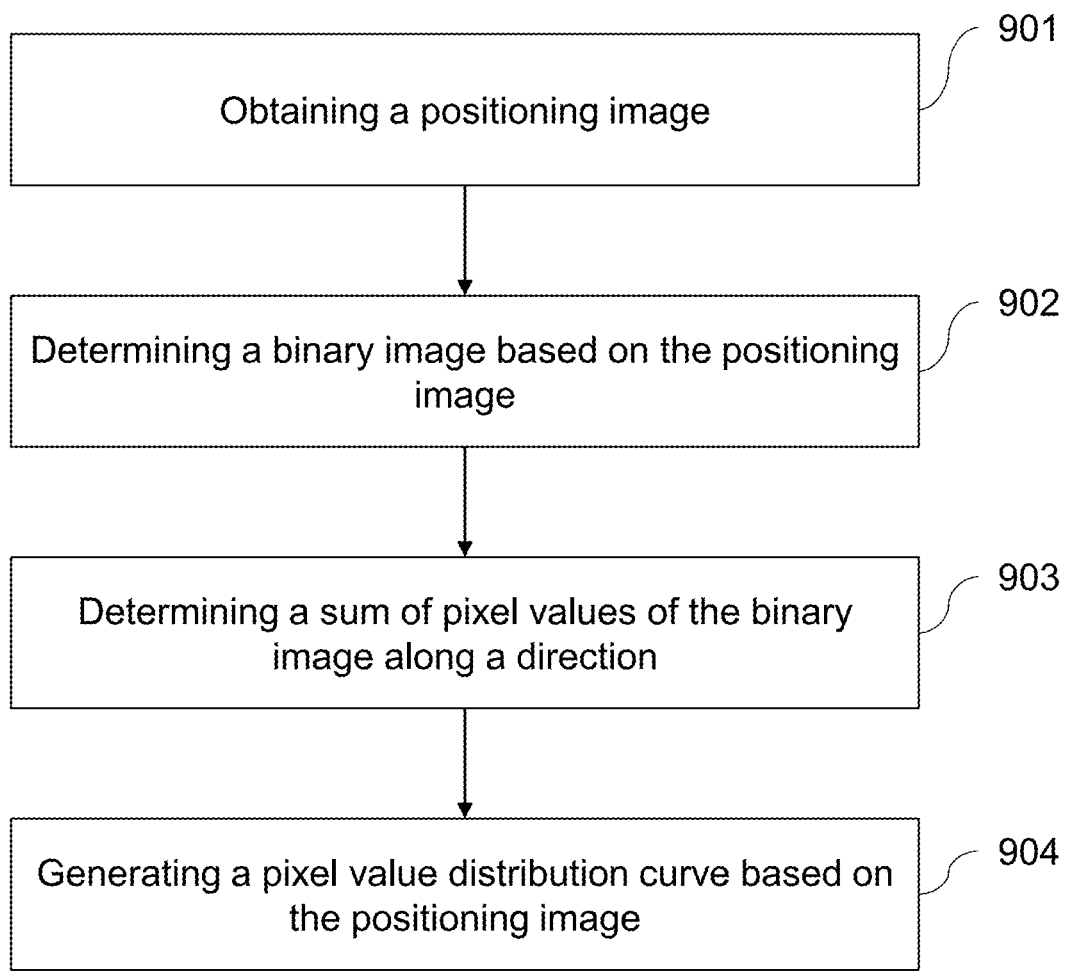
FIG. 9 is a flowchart illustrating another exemplary process of generating a pixel value distribution curve according to some embodiments of the present disclosure.

FIG. 9 is a flowchart illustrating another exemplary process of generating a pixel value distribution curve according to some embodiments of the present disclosure. The process 900 may be executed by the host computer 140. For example, the process 900 may be implemented as a set of instructions stored in the ROM 230 or the RAM 240. The processor 220 and/or the units 708-710 illustrated in FIG. 7 may execute the set of instructions, and when executing the instructions, the processor 220 and/or the units 708-710 may be configured to perform the process 900. The operations of the process 900 presented below are intended to be illustrative. In some embodiments, the process 900 may be accomplished with one or more additional operations not described and/or without one or more of the operations discussed. Additionally, the order in which the operations of the process illustrated in FIG. 9 and described herein is not intended to be limiting. In some embodiments, at least part of the operation 604 of the process 600 may be performed according to the process 900.

In 901, the host computer 140 (e.g., the binary image determination sub-unit 708, the interface circuits of the processor 220) may obtain a positioning image. The positioning image may be generated by the reconstruction unit 506. In some embodiments, the host computer 140 may obtain the positioning image from the reconstruction unit 506 and/or a storage device (e.g., the storage device 130, the storage module 440).

In 902, the host computer 140 (e.g., the binary image determination sub-unit 708, the interface circuits of the processor 220) may determine a binary image based on the positioning image. For example, the host computer 140 may compare each pixel value of the positioning image with a predetermined value (e.g., a background pixel value determined in 803). The host computer 140 may also modify the pixel values below the predetermined value to 0 and modify the pixel values that equal or exceed the predetermined value to 1.

In 903, the host computer 140 (e.g., the accumulation sub-unit 710, the processing circuits of the processor 220) may determine a sum of pixel values of the binary image along a direction. In some embodiments, the direction may include the direction of the X-axis shown in FIG. 16. For example, the host computer 140 may accumulate values of the pixels in a row of the binary image to generate the sum of pixel values of the row. The host computer 140 may also determine a plurality of sums of the pixel values of the binary image, and each of the plurality of sums corresponds to a row count of the binary image (i.e., the position of a row among the rows of the binary image).

In 904, the host computer 140 (e.g., the accumulation sub-unit 710, the processing circuits of the processor 220) may generate a pixel value distribution curve based on the positioning image. In some embodiments, the host computer 140 may generate the pixel value distribution curve of the binary image. For example, the host computer 140 may determine a graph by determining the sums of pixel values determined in 903 as the vertical axis "intensity," and determining the row count of the binary image as the horizontal axis "Z pixel index." Each of the plurality of sums and the corresponding row count may be a point in the graph. The host computer 140 may determine a curve based on a plurality of points in the graph, which is referred to herein as a pixel value distribution curve. Referring to FIG. 13, which illustrates an exemplary pixel value distribution curve, the Z pixel index represents the row count of the binary image, and the intensity represents the sum of pixel values of a row.

It should be noted that the above description is merely provided for illustration, and not intended to limit the scope of the present disclosure. For persons having ordinary skills in the art, multiple variations and modifications may be made under the teachings of the present disclosure. However, those variations and modifications do not depart from the scope of the present disclosure. For example, one or more other optional operations (e.g., a storing operation) may be added in the process 900. In the storing operation, the host computer 140 may store information and/or data associated with the positioning image, the binary image and the pixel value distribution curve in a storage device (e.g., the storage device 130, the storage module 440) as described elsewhere in the present disclosure.

FIG. 10 is a block diagram illustrating an exemplary second scan area determination unit according to some embodiments of the present disclosure. As illustrated in FIG. 10, the second scan area determination unit 510 may include a curvature determination sub-unit 1002, a curvature point determination sub-unit 1004, and a scan area determination sub-unit 1006.

The curvature determination sub-unit 1002 may be configured to determine curvature of a point of a pixel value distribution curve. In some embodiments, the curvature determination sub-unit 1002 may obtain a pixel value distribution curve from the distribution curve generation unit 508 or a storage (e.g., the storage device 130, the storage module 440). The curvature determination sub-unit 1002 may determine the curvature of any point in the pixel value distribution curve. For example, the curvature determination sub-unit 1002 may obtain a plurality of points from the pixel value distribution curve, and determine the curvatures of the plurality of points in the pixel value distribution curve. In some embodiments, the curvature determination sub-unit 1002 may perform filtering and/or noise reduction to the pixel value distribution curve before determine the curvatures of the plurality of points.

The curvature point determination sub-unit 1004 may be configured to determine one or more points from a plurality of points in the pixel value distribution curve. In some embodiments, the curvature point determination sub-unit 1004 may determine the one or more points from the plurality of points by comparing the curvatures of the plurality of points with a threshold curvature. For example, the curvature point determination sub-unit 1004 may compare the curvature of each of the plurality of points with the threshold curvature. The curvature point determination sub-unit 1004 may also determine the one or more points that have curvatures greater than the threshold curvature. In some embodiments, the threshold curvature may be determined by a user (e.g., a doctor) through the host computer 140 and/or the terminal 150.

The scan area determination sub-unit 1006 may be configured to determine a second scan area based on the one or more points determined by the curvature point determination sub-unit 1004. It should be noted that a point in the pixel value distribution curve may represent a row of a positioning image, and thus the point in the pixel value distribution curve may represent a boundary of an area in the positioning image (i.e., an area of the scanning object).

In some embodiments, the scan area determination sub-unit 1006 may determine the second scan area based on two points of the one or more points. For example, the scan area determination sub-unit 1006 may determine a first point of the two points as a first boundary. The scan area determination sub-unit 1006 may also determine a second point of the two points as the second boundary. The scan area determination sub-unit 1006 may further determine the area between the first boundary and the second boundary as the second scan area.

In some embodiments, the scan area determination sub-unit 1006 may determine the area between the first boundary and the second boundary as a sub-scan area. The scan area determination sub-unit 1006 may further determine one or more sub-scan areas as the second scan area.

In some embodiments, the scan area determination sub-unit 1006 may determine the second scan area based on a point of the one or more points and one edge of the positioning image. For example, the scan area determination sub-unit 1006 may determine the point as the first boundary. The scan area determination sub-unit 1006 may also determine the edge of the positioning image as the second boundary and determine the area between the first boundary and the second boundary as the second scan area.

In some embodiments, the scan area determination sub-unit 1006 may determine a scan distance based on the one or more points determined by the curvature point determination sub-unit 1004. As used herein, the scan distance may represent an actual distance of the object in the long axis direction between two boundaries determined by two points. The scan area determination sub-unit 1006 may also determine an organ of a human based on the scan distance. For example, the scan area determination sub-unit 1006 may determine a scan distance between two boundaries determined by two points of the one or more points. The scan area determination sub-unit 1006 may also determine the organ of the human according to a relation between the scan distance and the organ. In some embodiments, the relation between scan distance and organ may be obtained by experience and/or training samples. A relation lookup table between scan distance and organ may be generated previously. Further, the scan area determination sub-unit 1006 may determine the area between two boundaries determined by the two points as the second scan area or a sub-scan area.

The sub-units of the second scan area determination unit 510 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the sub-units may be combined into a single sub-unit, and any one of the sub-units may be divided into two or more sub-units. For example, the curvature point determination sub-unit 1004 and the scan area determination sub-unit 1006 may be combined into a single sub-unit that may be configured to determine one or more points that have curvatures greater than a threshold and determine a second scan area based on the one or more points.

Figure 11:
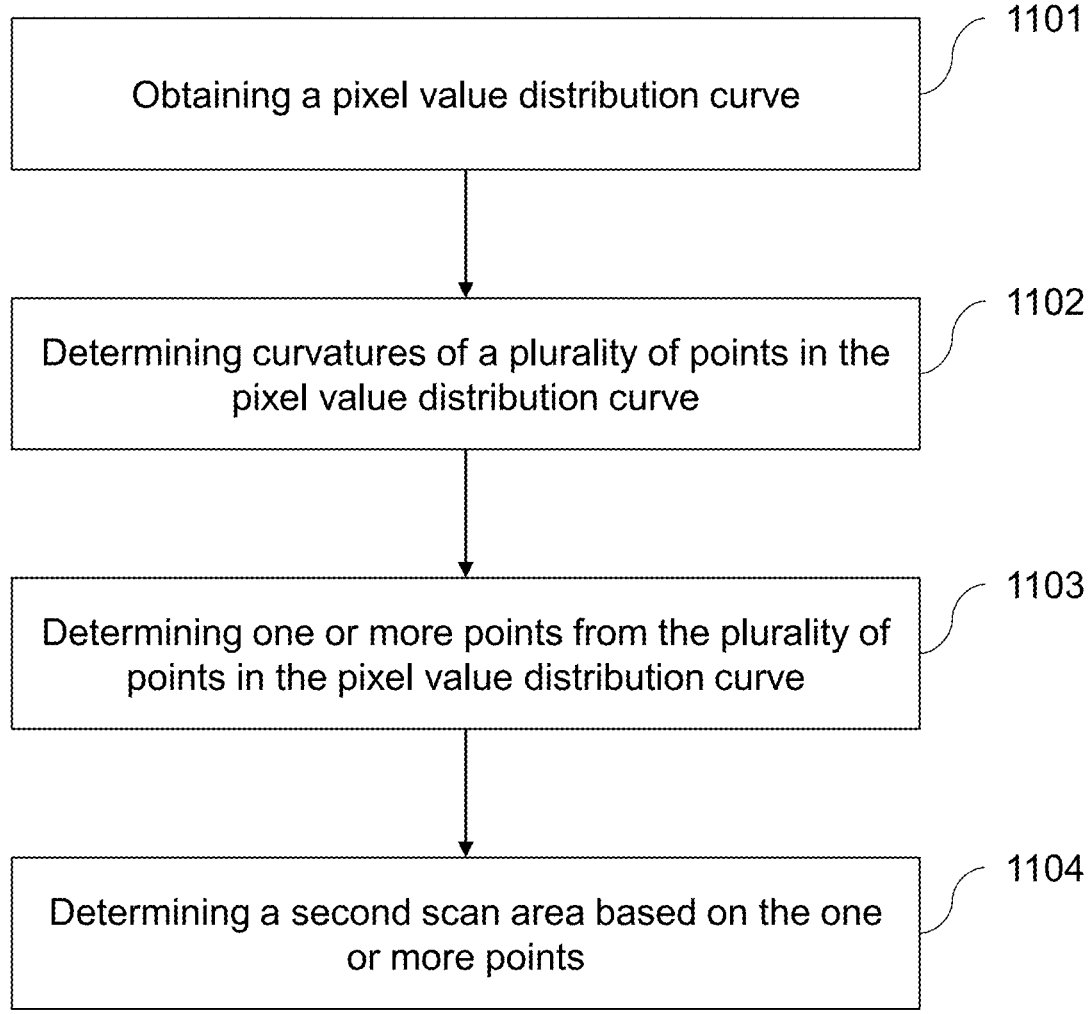
FIG. 11 is a flowchart illustrating an exemplary process of determining a second scan area according to some embodiments of the present disclosure.

FIG. 11 is a flowchart illustrating an exemplary process of determining a second scan area according to some embodiments of the present disclosure. The process 1100 may be executed by the host computer 140. For example, the process 1100 may be implemented as a set of instructions stored in the ROM 230 or the RAM 240. The processor 220 and/or the units 1002-1006 illustrated in FIG. 10 may execute the set of instructions, and when executing the instructions, the processor 220 and/or the units 1002-1006 may be configured to perform the process 1100. The operations of the process 1100 presented below are intended to be illustrative. In some embodiments, the process 1100 may be accomplished with one or more additional operations not described and/or without one or more of the operations discussed. Additionally, the order in which the operations of the process illustrated in FIG. 11 and described herein is not intended to be limiting. In some embodiments, at least part of the operation 605 of the process 600 may be performed according to the process 1100.

In 1101, the host computer 140 (e.g., the curvature determination sub-unit 1002, the interface circuits of the processor 220) may obtain a pixel value distribution curve. The pixel value distribution curve may be determined by the distribution curve generation unit 508. In some embodiments, the host computer 140 may obtain the pixel value distribution curve from the distribution curve generation unit 508 and/or a storage device (e.g., the storage device 130, the storage module 440).

Figure 14:
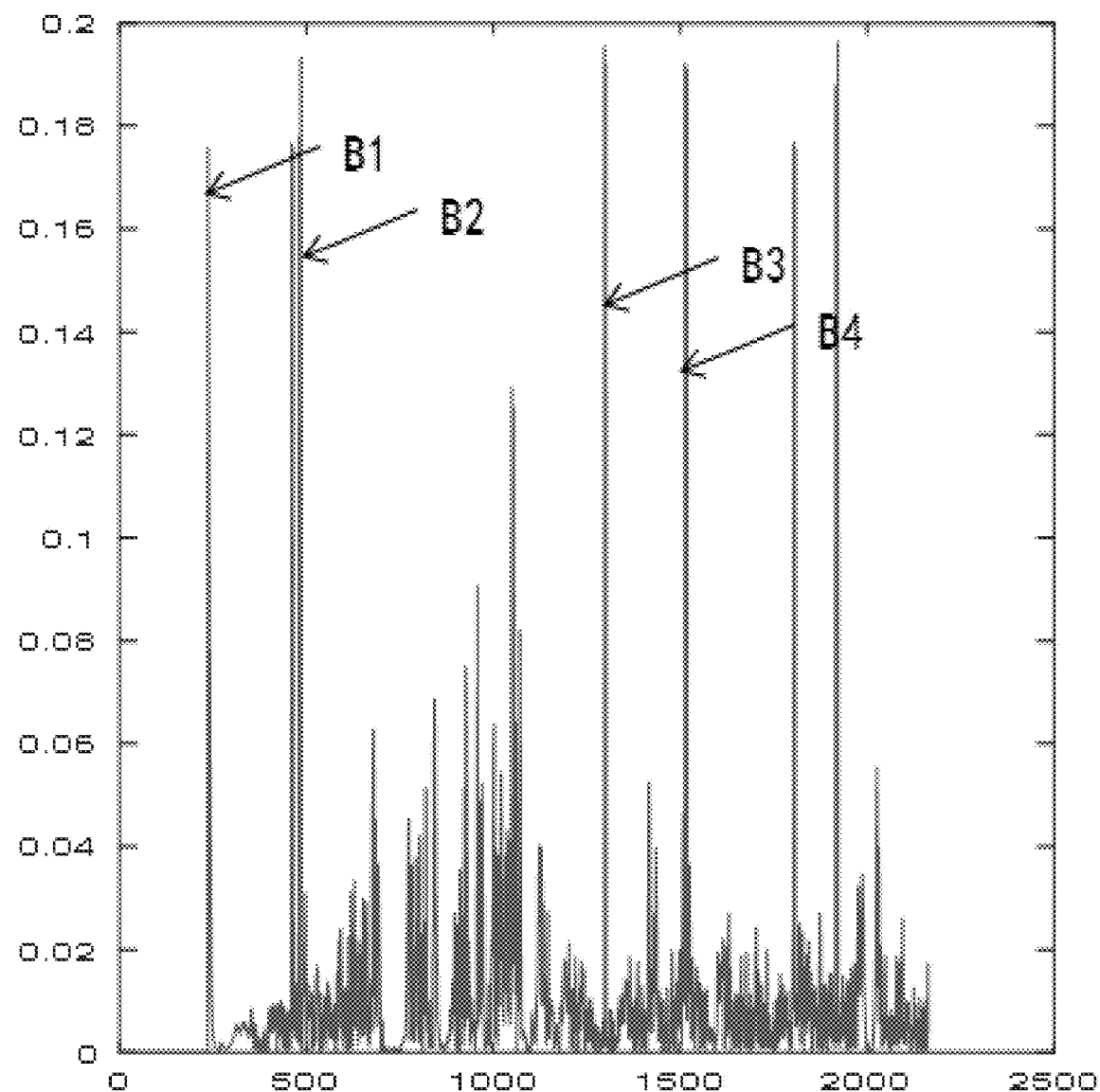
FIG. 14 is a graph illustrating an exemplary curvature of pixel value distribution curve according to some embodiments of the present disclosure.

In 1102, the host computer 140 (e.g., the curvature determination sub-unit 1002, the processing circuits of the processor 220) may obtain a plurality of points in the pixel value distribution curve and determine curvatures of the plurality of points in the pixel value distribution curve. As described elsewhere, a point in the pixel value distribution curve may represent a row count of a positioning image and a sum of pixel values of the row. The host computer 140 may determine a curvature for each of the points in the pixel value distribution curve. Each curvature may correspond to a row count. For illustration purpose, the curvatures of the points and the corresponding row counts thereof may be described in the same way (e.g., the description in operation 904) with respect to the pixel value distribution curve, as shown in FIG. 14. The horizontal axis may represent the row count of the positioning image, and the vertical axis may represent the curvature. In some embodiments, the host computer 140 may also perform filtering and/or noise reduction on the pixel value distribution curve before determining the curvatures of the plurality of points.

In 1103, the host computer 140 (e.g., the curvature point determination sub-unit 1004, the processing circuits of the processor 220) may determine one or more points from the plurality of points in the pixel value distribution curve determined in 1102. Different parts (e.g., the neck, lung, abdomen, buttocks and other regions) of a human body may have different pixel intensity in the pixel value distribution curve due to the composition and/or density thereof. The points correspond to the starting or ending of a human organ may have a high curvature. The position of the human organ (e.g., a start position or an end position of the head, neck, lung, and abdomen) in the positioning image may be obtained by comparing the curvature of points in the pixel value distribution curve with a threshold curvature and determining one or more points based on the comparison.

In some embodiments, the host computer 140 may determine the one or more points from the plurality of points by comparing the curvatures of the plurality of points with a threshold curvature. For example, the host computer 140 may compare the curvature of each of the plurality of points with the threshold curvature. The host computer 140 may also determine that one or more points have a curvature that is greater than the threshold curvature. Merely by way of example, as shown in FIG. 14, the host computer 140 may determine that points B1, B2, B3, and B4 have a curvature that is greater than the threshold curvature (e.g., 0.17). Point B1 may represent the start of the head, the point B2 may represent the end of the head and/or the start of the neck, the point B3 may represent the start of the abdomen, and the point B4 may represent the end of the abdomen. In some embodiments, the threshold curvature may be determined by a user (e.g., a doctor) according to a predetermined scan area, which may be determined according to an input by a user through, for example, an input device of the host computer 140 and/or the terminal 150.

In 1104, the host computer 140 (e.g., the scan area determination sub-unit 1006, the processing circuits of the processor 220) may determine a second scan area based on the one or more points determined in 1103. In some embodiments, the host computer 140 may determine the second scan area based on two points (e.g., points B1 and B2 shown in FIG. 14) of the points. For example, the host computer 140 may determine a first point (e.g., point B1 shown in FIG. 14) of the two points as a first boundary. The host computer 140 may also determine a second point (e.g., point B2 shown in FIG. 14) of the two points as the second boundary. The host computer 140 may further determine the area between the first boundary and the second boundary (e.g., the head) as the second scan area.

In some embodiments, the host computer 140 may determine the area between the first boundary and the second boundary as a sub-scan area. The host computer 140 may determine one or more sub-scan areas as the second scan area. For example, the host computer 140 may determine the area between points B1 and B2 shown in FIG. 14 as a first sub-scan area. The host computer 140 may also determine the area between points B3 and B4 shown in FIG. 14 as a second sub-scan area and determine the first sub-scan area and the second sub-scan area as the second scan area.

In some embodiments, the host computer 140 may determine the second scan area between one point of the one or more points and one edge of the positioning image. For example, the host computer 140 may determine the point (e.g., point B1 shown in FIG. 14) as the first boundary. The host computer 140 may also determine the edge of the positioning image as the second boundary and determine the area between the first boundary and the second boundary as the second scan area.

In some embodiments, the host computer 140 may determine a scan distance based on the one or more points determined in 1103. The host computer 140 may also determine an organ of a human based on the scan distance. For example, the host computer 140 (e.g., the scan area determination sub-unit 1006) may determine a scan distance between two boundaries determined by two points of the one or more points determined in 1103. The host computer 140 may also determine the organ of a human based on the scan distance according to a relation lookup table between the scan distance and the organ. In some embodiments, at least part of the relation lookup table between the scan distances and the organs (or tissue) may be predetermined according to input by a user through, for example, an input device of the host computer 140 and/or the terminal 150.

Merely by way of example, if the scan distance between two points in the axial direction is 10 cm, the scan area determination sub-unit 1006 may determine the organ between two boundaries determined by the two points is heart. The host computer 140 may further determine the area between the two boundaries determined by the two points as the second scan area or a sub-scan area. If the scan distance between two points is 12 cm, the scan area determination sub-unit 1006 may determine that there is no organ corresponding to the scan distance. The host computer 140 may replace at least one point of the two points with a third point from the one or more points. The host computer 140 may determine a new scan distance based on the replaced points.

It should be noted that the above description is merely provided for illustration, and not intended to limit the scope of the present disclosure. For persons having ordinary skills in the art, multiple variations and modifications may be made under the teachings of the present disclosure. However, those variations and modifications do not depart from the scope of the present disclosure. For example, one or more other optional operations (e.g., a storing operation) may be added in the process 1100. In the storing operation, the host computer 140 may store information and/or data associated with the pixel value distribution curve, the curvatures of a plurality of points in a storage device (e.g., the storage device 130, the storage module 440) as described elsewhere in the present disclosure.

FIG. 12 is a graph illustrating an exemplary pixel value distribution histogram according to some embodiments of the present disclosure. An image may include a plurality of pixels, and each of the plurality of pixels has a pixel value. The host computer 140 may count the number of pixels have same pixel value, and generate statistics of the pixel values of the image. The host computer 140 may further generate a pixel value distribution histogram based on the statistics. As shown in FIG. 12, the horizontal axis represents the pixel value, e.g., in a range of 0-1600, and the vertical axis represents the number of pixels. Each point in the graph may represent a pixel value and corresponding pixel number. For example, the peak A in the graph may represent that the number of pixel having the pixel value 590 is more than 100,000.

FIG. 13 is a graph illustrating an exemplary pixel value distribution curve according to some embodiments of the present disclosure. An image may have a resolution, which represents the number of rows and the number of columns. For example, a positioning image shown in FIG. 16 may have a resolution of 700*2200, which means that the positioning image has 700 columns and 2500 rows. And each row has 700 pixels, each column has 2200 pixels. The host computer 140 may determine a sum of pixel values of each row or column. The host computer 140 may further generate a pixel value distribution curve based on the sums of pixel values and the corresponding row count. As shown in FIG. 13, the vertical axis represents intensity, i.e., the sum of pixel values. The horizontal axis represents Z pixel index, i.e., the row count, e.g., from 1 to 2200. Each point in the pixel value distribution curve may represent a row count and corresponding sum of pixel values of the row.

FIG. 14 is a graph illustrating an exemplary curvature of pixel value distribution curve according to some embodiments of the present disclosure. As described elsewhere, a point in a pixel value distribution curve shown in FIG. 13 may represent a row count of a positioning image and a sum of pixel values of the row. The host computer 140 may determine a curvature for each of the points in the pixel value distribution curve. Each curvature may correspond to a row count. The host computer 140 may generate a graph of curvature of pixel value distribution curve based on the curvature and the corresponding row count. As shown in FIG. 14, the horizontal axis may represent the row count of the positioning image, and the vertical axis may represent the curvature.

Figure 15:
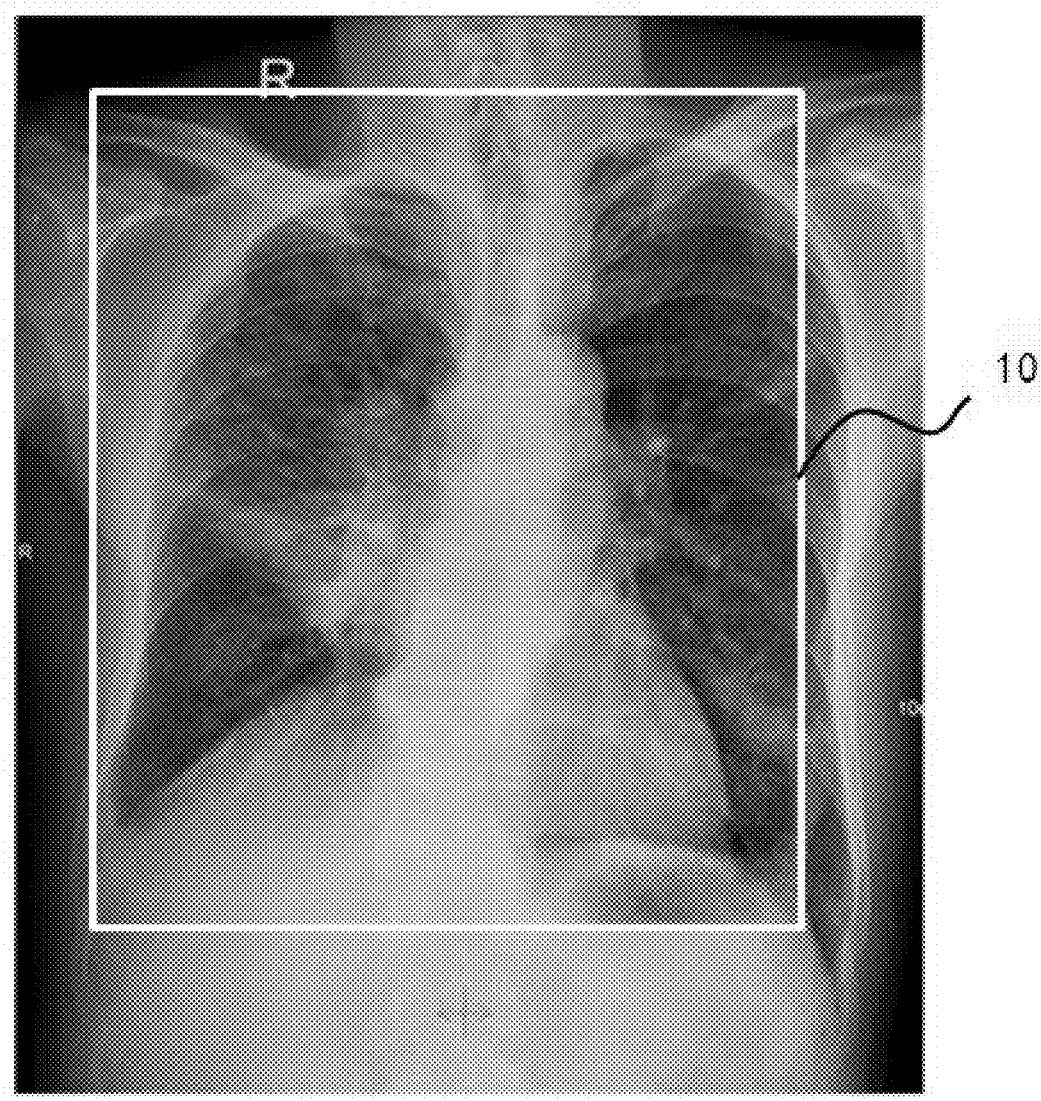
FIG. 15 is a graph illustrating an exemplary positioning image according to some prior art designs.

FIG. 15 is a graph illustrating an exemplary positioning image according to some prior art designs. As shown in FIG. 15, the positioning image may include chest of a patient. On the interface where the positioning image is displayed, a rectangular frame representing a scan area 10 is drawn on the positioning image by dragging a mouse. After dragging, the scan area 10 is determined. Parts to be examined may be in the second scan area and the system may perform scanning and reconstruction based on the second scan area thus the rest of the patient may be free from scanning.

FIG. 16 is a graph illustrating an exemplary positioning image according to some embodiments of the present disclosure. As shown in FIG. 16, the positioning image may include head and torso of a patient. The Z-axis may represent the long axis of the patient, the X-axis may represent a direction in the coronal plane of the patient and perpendicular to the Z-axis. The positioning image shown in FIG. 16 may be used to determine a second scan area according to the methods disclosed in the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A computer-readable signal medium may include a propagated data signal with computer-readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

I claim:

1. A system for determining a scan area, comprising:
at least one storage device storing a set of instructions; and
at least one processor in a communication with the at least one storage device, wherein when executing the set of instructions, the at least one processor is configured to perform operations including:
acquiring a positioning image of an object, wherein the positioning image includes pixels arranged in multiple rows;
determining multiple sums, each of which includes a sum of pixel values of pixels in each row of the multiple rows in the positioning image;
generating a pixel value distribution curve based on the multiple sums and respective rows of the multiple rows in the positioning image;
determining, based on the pixel value distribution curve, a scan area on the object; and
causing a scanner to scan the scan area on the object.

2. The system of claim 1, wherein the multiple rows are along a direction perpendicular to a long axis direction of the object.

3. The system of claim 1, wherein to determine multiple sums, each of which includes a sum of pixel values of pixels in each row of the multiple rows in-the positioning image, the at least one processor is configured to perform the operations including:
determining a background pixel value of the positioning image;
determining a reduced image by subtracting the background pixel value of the positioning image from a pixel value of each pixel of at least some pixels in the positioning image, the reduced image including pixels arranged in multiple rows; and
determining a sum of pixel values of pixels in each row of the multiple rows in the reduced image.

4. The system of claim 3, wherein to determine a background pixel value of the positioning image, the at least one processor is configured to perform the operations including:
determining a pixel value distribution histogram of the positioning image; and
determining, based on the pixel value distribution histogram, the background pixel value, wherein the background pixel value of the positioning image includes a pixel value of a peak in the pixel value distribution histogram.

5. The system of claim 3, wherein to determine a background pixel value of the positioning image, the at least one processor is configured to perform the operations including:
determining, based on a sample database, the background pixel value of the positioning image.

6. The system of claim 1, wherein to determine multiple sums, each of which includes a sum of pixel values of pixels in each row of the multiple rows in the positioning image, the at least one processor is configured to perform the operations including:

determining a binary image based on the positioning image, the binary image including pixels arranged in multiple rows; and determining a sum of pixel values of pixels in each row of the multiple rows in the binary image.

7. The system of claim 6, wherein to determine a binary image based on the positioning image, the at least one processor is configured to perform the operations including:

comparing each pixel value of the positioning image with a predetermined value; and generating the binary image by modifying pixels of the positioning image having pixel value below the predetermined value to 0 and modifying the pixels of the positioning image having pixel value greater than the predetermined value to 1.

8. The system of claim 7, wherein the predetermined value includes a background pixel value of the positioning image.

9. The system of claim 1, wherein to determine a scan area on the object based on the pixel value distribution curve, the at least one processor is configured to perform the operations including:

determining curvatures of a plurality of points in the pixel value distribution curve;

determining one or more points from the plurality of points in the pixel value distribution curve that have curvatures greater than a threshold curvature; and determining the scan area on the object based on the one or more points.

10. The system of claim 9, wherein to determine the scan area on the object based on the one or more points, the at least one processor is configured to perform the operations including:

determining a first boundary and a second boundary of the scan area on the object based on the one or more points.

11. The system of claim 9, wherein:

the scan area on the object includes one or more sub-scan areas; and to determine the scan area on the object based on the one or more points, the at least one processor is configured to perform the operations including:

determining a first boundary and a second boundary of each sub-scan area of the one or more sub-scan areas based on the one or more points.

12. The system of claim 9, wherein to determine the scan area on the object based on the one or more points, the at least one processor is configured to perform the operations including:

determining the scan area on the object based on a point of the one or more points and one edge of the positioning image.

13. A method implemented on at least one machine, each machine of the at least one machine having at least one processor and at least one storage device, comprising:

acquiring, by the at least one processor, a positioning image of an object, wherein the positioning image includes pixels arranged in multiple rows;

determining, by the at least one processor, multiple sums, each of which includes a sum of pixel values of pixels in each row of the multiple rows in the positioning image;

generating, by the at least one processor, a pixel value distribution curve based on the multiple sums and respective rows of the multiple rows in the positioning image;

determining, by the at least one processor, a scan area on the object based on the pixel value distribution curve; and causing, by the at least one processor, a scanner to scan the scan area on the object.

14. The method of claim 13, wherein the multiple rows are along a direction perpendicular to a long axis direction of the object.

15. The method of claim 13, wherein determining, by the as least one processor, multiple sums, each of which includes a sum of pixel values of pixels in each row of the multiple rows in the positioning image comprises:

determining, by the at least one processor, a background pixel value of the positioning image;

determining, by the at least one processor, a reduced image by subtracting the background pixel value of the positioning image from a pixel value of each pixel of at least some pixels in the positioning image, the reduced image including pixels arranged in multiple rows; and determining, by the at least one processor, a sum of pixel values of pixels in each row of the multiple rows in the reduced image.

16. The method of claim 15, wherein to determine, by the at least one processor, a background pixel value of the positioning image comprises:

determining, by the at least one processor, the background pixel value of the positioning image based on a sample database.

17. The method of claim 13, wherein determining, by the at least one processor, multiple sums, each of which includes a sum of pixel values of pixels in each row of the multiple rows in the positioning image comprises:

determining, by the at least one processor, a binary image based on the positioning image, the binary image including pixels arranged in multiple rows; and determining, by the at least one processor, a sum of pixel values of pixels in each row of the multiple rows in the binary image.

18. The method of claim 13, wherein determining, by the at least one processor, a scan area on the object based on the pixel value distribution curve comprises:

determining, by the at least one processor, curvatures of a plurality of points in the pixel value distribution curve;

determining, by the at least one processor, one or more points of the plurality of points in the pixel value distribution curve that have curvatures greater than a threshold curvature; and determining, by the at least one processor, the scan area on the object based on the determined one or more points.

19. The method of claim 18, wherein to determine, by the at least one processor, the scan area on the object based on the one or more points comprises:

determining, by the at least one processor, the scan area on the object based on a point of the one or more points and one edge of the positioning image.

20. A non-transitory computer-readable medium storing instructions, the instructions, when executed by a computing device, causing the computing device to implement a method, the computing device including at least one processor, the method comprising:

acquiring, by the at least one processor, a positioning image of an object, wherein the positioning image includes pixels arranged in multiple rows;

determining, by the at least one processor, multiple sums, each of which includes a sum of pixel values of pixels in each row of the multiple rows in the positioning image;

generating, by the at least one processor, a pixel value distribution curve based on the multiple sums and respective rows of the multiple rows in the positioning image;

determining, by the at least one processor, a scan area on the object based on the pixel value distribution curve; and causing, by the at least one processor, a scanner to scan the scan area on the object.

* * * * *